US009199945B2

(12) United States Patent
Oslob et al.

(10) Patent No.: US 9,199,945 B2
(45) Date of Patent: Dec. 1, 2015

(54) CYCLOALKYL-SUBSTITUTED PYRIMIDINEDIONE COMPOUNDS

(71) Applicant: MyoKardia, Inc., South San Francisco, CA (US)

(72) Inventors: Johan Oslob, Sunnyvale, CA (US); Robert Anderson, Brisbane, CA (US); Danielle Aubele, San Mateo, CA (US); Marc Evanchik, San Jose, CA (US); Jonathan Charles Fox, San Francisco, CA (US); Brian Kane, Oakland, CA (US); Robert McDowell, San Francisco, CA (US); Hector Rodriguez, Brisbane, CA (US); Yonghong Song, Foster City, CA (US); Arvinder Sran, Foster City, CA (US); Pu-Ping Lu, South San Francsico, CA (US)

(73) Assignee: Myokardia, Inc., South San Francisco, CA (US)

( * ) Notice: Subject to any disclaimer, the term of this patent is extended or adjusted under 35 U.S.C. 154(b) by 0 days.

(21) Appl. No.: 14/309,414

(22) Filed: Jun. 19, 2014

(65) Prior Publication Data

US 2014/0378491 A1 Dec. 25, 2014

Related U.S. Application Data

(60) Provisional application No. 61/838,096, filed on Jun. 21, 2013, provisional application No. 61/939,652, filed on Feb. 13, 2014.

(51) Int. Cl.
| | |
|---|---|
| *C07D 239/545* | (2006.01) |
| *A61K 31/513* | (2006.01) |
| *A61K 45/06* | (2006.01) |
| *C07D 403/04* | (2006.01) |
| *C07D 405/04* | (2006.01) |

(52) U.S. Cl.
CPC .......... *C07D 239/545* (2013.01); *A61K 31/513* (2013.01); *A61K 45/06* (2013.01); *C07D 403/04* (2013.01); *C07D 405/04* (2013.01)

(58) Field of Classification Search
CPC .............. C07D 401/04; C07D 403/04; C07D 239/545; C07D 405/04; C07D 239/553; C07D 401/12; C07D 403/12; C07D 413/04; C07D 405/12; A61K 31/513; A61K 45/06
See application file for complete search history.

(56) References Cited

U.S. PATENT DOCUMENTS

| | | | |
|---|---|---|---|
| 5,516,905 | A | 5/1996 | Brown et al. |
| 6,174,941 | B1 | 1/2001 | Wehner et al. |
| 6,495,337 | B1 | 12/2002 | Hartman et al. |
| 6,509,167 | B1 | 1/2003 | Hartman et al. |
| 6,573,061 | B1 | 6/2003 | Hartman et al. |
| 6,759,240 | B1 | 7/2004 | Hartman et al. |
| 7,160,893 | B2 | 1/2007 | Hicks et al. |
| 7,202,051 | B1 | 4/2007 | Finer et al. |
| 7,214,503 | B2 | 5/2007 | Hartman et al. |
| 7,416,856 | B2 | 8/2008 | Baliga et al. |
| 7,781,584 | B2 | 8/2010 | Feng et al. |
| 7,824,880 | B2 | 11/2010 | Baliga et al. |
| 2003/0114414 | A1 | 6/2003 | Zhi et al. |
| 2005/0186640 | A1* | 8/2005 | Marks et al. ................... 435/7.2 |
| 2009/0163545 | A1* | 6/2009 | Goldfarb ....................... 514/312 |
| 2014/0378464 | A1* | 12/2014 | Oslob et al. .............. 514/252.02 |

FOREIGN PATENT DOCUMENTS

| | | |
|---|---|---|
| CA | 2038198 A1 * | 9/1991 |
| DE | 1280877 A2 * | 10/1968 |
| DE | 1280877 B | 10/1968 |
| EP | 0447324 A1 | 9/1991 |
| EP | 447324 A1 * | 9/1991 |
| JP | 61205261 A2 | 9/1986 |
| WO | 96/06614 A1 | 3/1996 |
| WO | 01/29010 A1 | 4/2001 |
| WO | 02/102769 A2 | 12/2002 |
| WO | 2004/014868 A2 | 2/2004 |
| WO | 2005/095381 A1 | 10/2005 |
| WO | 2006/089221 A2 | 8/2006 |

OTHER PUBLICATIONS

STN CAS Registry Nos. (2010).*
STN CAS Registry Nos. (2006).*
STN CAS Registry Nos. (2005).*
H. Yan et al., 20 Journal of Chinese Pharmaceutical Sciences, 146-153 (2011).*
C. Mueller et al., 36 Journal of Medicinal Chemistry, 3341-3349 (1993).*
P. Singh et al., 14 Bioorganic & Medicinal Chemistry, 7183-7186 (2006).*
P. Singh et al., 14 Bioorganic & Medicinal Chemistry, 8622-8625 (2006).*
G. Liu et al., 40 Synthetic Communications, 1418-1436 (2010).*
CAS Abstract of EP 447,324 (1991).*
CAS Abstract of DE 1,280,877 (1969).*
Liu et al., "Synthesis of Novel 3,7-Dihydro-Purine-2,6-Dione Derivatives," Synthetic Communications, 2010, vol. 40(10), pp. 1418-1436.
Muller et al., "Synthesis of Paraxanthine Analogs (1,7-Disubstituted Xanthines) and Other Xanthines Unsubstituted at the 3-Position: Structure-Activity Relationship at Adenosine Receptors," J. Med. Chem, 1993, vol. 36, pp. 3341-3349.
International Search Report and Written Opinion, Sep. 29, 2014 PCT application No. PCT/US2014/043210, 8 pages.
National Institute of Allergy and Infectious Diseases—Division of AIDS Anti-HIV/OI/TB Therapeutics Database—Details Page, "AIDS#: 147565," Last Updated: Apr. 2014 (2 pages).

(Continued)

*Primary Examiner* — Alexander R Pagano
(74) *Attorney, Agent, or Firm* — Kilpatrick Townsend & Stockton LLP; William B. Kezer

(57) ABSTRACT

The present invention provides novel cycloalkyl-substituted pyrimidine dione compounds that are useful for the treatment of hypertrophic cardiomyopathy (HCM) and conditions associated with left ventricular hypertrophy or diastolic dysfunction. The synthesis and characterization of the compounds is described, as well as methods for treating HCM and other forms of heart disease.

20 Claims, 1 Drawing Sheet

(56) References Cited

OTHER PUBLICATIONS

Dimoglo, A. S. et al., "Influence of Structural and Electronic Properties of Uranyl Derivatives on the Inhibition of Thymidine Phosphorylase," *Institute of Chemistry, Academy of Sciences of the Moldavian SSR, Kishinev*, pp. 628-636 © 1986 Plenum Publishing Corporation. Translated from Khimikofarmatsevticheskii Zhurnal, 19(9):1086-1096 (Sep. 1985). Original article submitted Jul. 3, 1984.

* cited by examiner

A
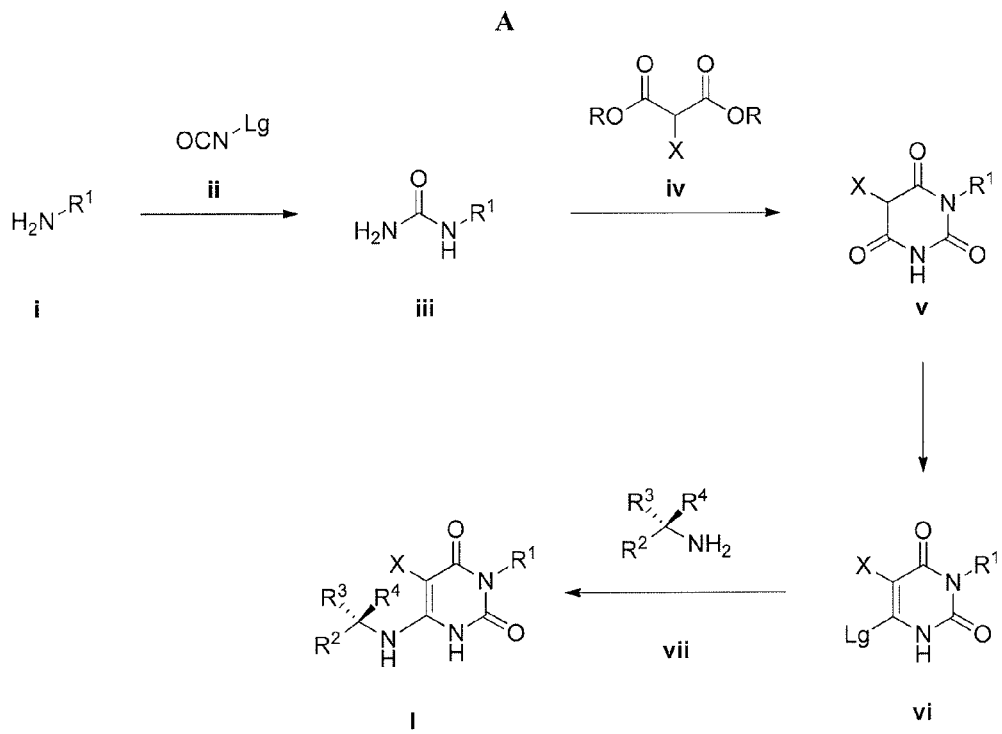
B
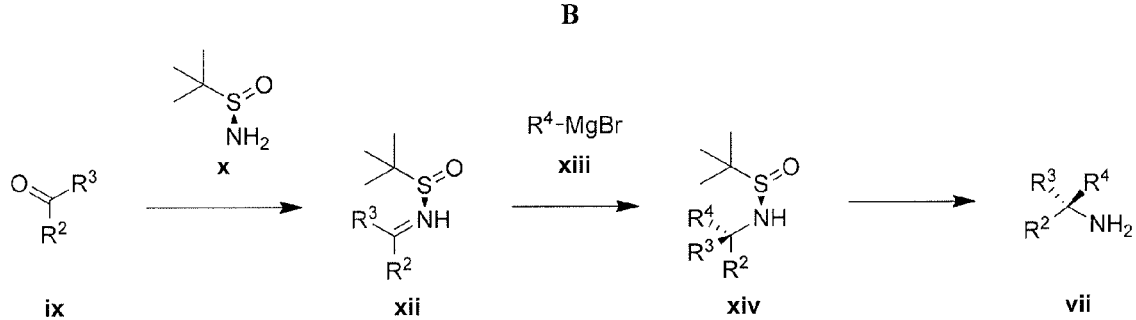

CYCLOALKYL-SUBSTITUTED PYRIMIDINEDIONE COMPOUNDS

CROSS-REFERENCES TO RELATED APPLICATIONS

This application is an application claiming benefit under 35 U.S.C. §119(e) of U.S. Provisional Application No. 61/838,096 filed Jun. 21, 2013, and U.S. Provisional Application No. 61/939,652 filed Feb. 13, 2014, each of which is herein incorporated by reference in its entirety.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

Genetic (heritable) hypertrophic cardiomyopathy (HCM) comprises a group of highly penetrant, monogenic, autosomal dominant myocardial diseases. HCM is caused by one or more of over 1,000 known point mutations in any one of the structural protein genes contributing to the functional unit of myocardium, the sarcomere. About 1 in 500 individuals in the general population are found to have left ventricular hypertrophy unexplained by other known causes (e.g., hypertension or valvular disease), and many of these can be shown to have HCM, once other heritable (e.g., lysosomal storage diseases), metabolic, or infiltrative causes have been excluded.

Sarcomere gene mutations that cause HCM are highly penetrant, but there is wide variability in clinical severity and clinical course. Some genotypes are associated with a more malignant course, but there is considerable variability between and even within families carrying the same mutation. Sex differences have also been noted, with male patients generally more severely affected than female patients. While many patients with HCM report minimal or no symptoms for extended periods of time, HCM is a progressive disease with a significant cumulative burden of morbidity. Symptoms of effort intolerance predominate, and can be exacerbated by exercise and other maneuvers that increase heart rate and/or decrease preload. As with many other disorders, symptoms tend to worsen with age. By far the most prevalent clinical burden for patients with HCM is exertional dyspnea, which limits their activities of daily living and can be debilitating.

Patients with HCM are often symptomatic in the absence of documented hemodynamic abnormalities like left ventricular outflow tract obstruction (with or without mitral regurgitation). Patients' symptoms of exertional dyspnea can rapidly worsen with the onset of atrial fibrillation, a common complication of HCM that can precipitate acute pulmonary edema and increases the risk of systemic arterial thromboembolic disease, including stroke. Other adverse events associated with HCM include intolerance of hypovolemia or hypervolemia, and syncope. Concomitant coronary artery disease may confer a higher risk of acute coronary syndromes than in patients without HCM. Sudden cardiac death (SCD) in patients with HCM is both uncommon and difficult to predict but is a leading cause of non-traumatic death in young adults. For survivors of SCD, ICD placement is standard practice, and in other HCM patients risk profiling, while imprecise, is used to identify those for whom ICD placement for primary prevention is deemed prudent.

Medical therapy for HCM is limited to the treatment of symptoms and does not address the fundamental, underlying cause of disease—disruptions in normal sarcomere function. Currently available therapies are variably effective in alleviating symptoms but typically show decreased efficacy with increasing disease duration. Patients are thus empirically managed with beta-blockers, non-dihydropyridine calcium channel blockers, and/or disopyramide. None of these agents carry labeled indications for treating HCM, and essentially no rigorous clinical trial evidence is available to guide their use. Compounding this unfortunate situation is the fact that no new medical therapies for HCM have been identified for many years. For patients with hemodynamically significant outflow tract obstruction (resting gradient>30 mmHg), in appropriately selected patients surgical myectomy or alcohol septal ablation is usually required to alleviate the hemodynamic obstruction. The present invention provides new therapeutic agents and methods that remedy the long-felt need for improved treatment of HCM and related cardiac disorders.

BRIEF SUMMARY OF THE INVENTION

In one aspect, provided is a compound having the formula:

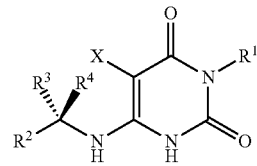

or a pharmaceutically acceptable salt thereof. In some embodiments, $R^1$ can be $C_1$-$C_8$ alkyl, $C_3$-$C_8$ cycloalkyl, 4- to 7-membered heterocycloalkyl, phenyl, or 5- to 6-membered heteroaryl, wherein each $R^1$ is optionally substituted with from 1-3 $R^a$. $R^2$ can be $C_3$-$C_8$ cycloalkyl, $C_3$-$C_8$ cycloalkyl $C_1$-$C_3$ alkyl, or 4- to 7-membered heterocycloalkyl, wherein each $R^2$ is optionally substituted with from 1-5 $R^b$. $R^3$ can be H, $C_1$-$C_4$ alkyl, $C_3$-$C_4$ cycloalkyl, or 4- to 7-membered heterocycloalkyl wherein each $R^3$ is optionally substituted with from 1-2 $R^c$. $R^4$ can be H or $C_1$-$C_4$ alkyl. Optionally, $R^3$ and $R^4$ can be combined with the carbon atom to which each is attached to form a 3- or 4-membered cycloalkyl or heterocycloalkyl ring. In some embodiments, at least one of $R^3$ and $R^4$ is other than H. X can be H or F. Each $R^a$ can independently be halo, CN, $C_1$-$C_4$ alkyl, $C_1$-$C_4$ alkoxy, —$COR^{a1}$, —$CO_2R^{a1}$, —$SO_2R^{a1}$, —$SO_2NR^{a1}R^{a2}$, or —$CONR^{a1}R^{a2}$, wherein each $R^{a1}$ and $R^{a2}$ can independently be H and $C_1$-$C_4$ alkyl. In other embodiments, $R^{a1}$ and $R^{a2}$ when attached to a nitrogen atom can be combined to form a 4- to 6-membered ring. Each $R^b$ can independently be halo, CN, $C_1$-$C_4$ alkyl, $C_1$-$C_4$ alkoxy, —$COR^{b1}$, —$CO_2R^{b1}$, —$SO_2R^{b1}$, —$SO_2NR^{b1}R^{b2}$, or —$CONR^{b1}R^{b2}$, wherein each $R^{b1}$ and $R^{b2}$ can independently be H or $C_1$-$C_4$ alkyl. Alternatively, $R^{b1}$ and $R^{b2}$ when attached to a nitrogen atom can be combined to form a 4- to 6-membered ring. Each $R^c$ can independently be halo or $C_1$-$C_2$ alkoxy.

In another aspect, the invention provides a pharmaceutical composition containing a compound or a pharmaceutically acceptable salt thereof as described herein and a pharmaceutically acceptable excipient.

In another aspect, the invention provides a method of treating hypertrophic cardiomyopathy. The method includes administering to a subject in need thereof an effective amount of a compound or pharmaceutically acceptable salt thereof as described herein.

BRIEF DESCRIPTION OF THE DRAWINGS

FIG. 1 shows a schematic route for the synthesis of the compounds or pharmaceutically acceptable salts described herein (FIG. 1A) and a route for the preparation of chiral amines (FIG. 1B).

DETAILED DESCRIPTION OF THE INVENTION

I. General

A series of cycloalkyl-substituted pyrimidine dione compounds has been found to reduce excess contractility in hypercontractile states and/or promote cardiac relaxation in hearts with diastolic dysfunction by stabilizing the conformation of beta cardiac myosin post-ATP hydrolysis but prior to strongly binding the actin filament and releasing phosphate, thus reducing the proportion of myosin molecules that are available to participate in the "powerstroke" portion of the muscle contraction cycle. As such, the compounds can improve cardiac elasticity, reduce dynamic and/or static left ventricular outflow obstruction, improve diastolic left ventricular relaxation, reduce left ventricular diastolic (filling) pressures, reduce functional mitral regurgitation, and/or reduce left atrial and pulmonary capillary wedge pressures in patients with HCM helping overcome the debilitating exertional dyspnea and/or symptoms referable to left ventricular outflow obstruction (presyncope or syncope) that often accompanies the disease. The compounds can also be used to treat other cardiac disorders.

II. Definitions

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Unless stated otherwise, alkyl groups are unsubstituted. A "substituted alkyl" group can be substituted with one or more moieties selected from halo, hydroxy, amino, alkylamino, nitro, cyano, and alkoxy.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Unless otherwise stated, cycloalkyl groups are unsubstituted. A "substituted cycloalkyl" group can be substituted with one or more moieties selected from halo, hydroxy, amino, alkylamino, nitro, cyano, and alkoxy.

As used herein, the term "heterocycloalkyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocycloalkyl groups can include any number of ring atoms, such as, 3 to 6, 4 to 6, 5 to 6, or 4 to 7 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Examples of heterocycloalkyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocycloalkyl groups are unsubstituted, but can be described, in some embodiments as substituted. "Substituted heterocycloalkyl" groups can be substituted with one or more moieties selected from halo, hydroxy, amino, alkylamino, nitro, cyano, and alkoxy.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 5 to 6, 5 to 8, 6 to 8, 5 to 9, 5 to 10, 5 to 11, or 5 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. Heteroaryl groups are unsubstituted, but can be described, in some embodiments as substituted. "Substituted heteroaryl" groups can be substituted with one or more moieties selected from halo, hydroxy, amino, alkylamino, nitro, cyano, and alkoxy.

As used herein, the term "alkoxy" refers to an alkyl group having an oxygen atom that connects the alkyl group to the point of attachment: i.e., alkyl-O—. As for the alkyl portions, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups are unsubstituted, but can be described, in some embodiments as substituted. "Substituted alkoxy" groups can be substituted with one or more moieties selected from halo, hydroxy, amino, alkylamino, nitro, cyano, and alkoxy.

As used herein, the terms "halo" and "halogen" refer to fluorine, chlorine, bromine and iodine.

As used herein, the term "pharmaceutically acceptable" refers to a substance that is compatible with a compound of the invention, as well as with any other ingredients with which the compound is formulated. Furthermore, a pharmaceutically acceptable substance is not deleterious to the recipient of the substance.

As used herein, the term "salt" refers to an acid or base salt of a compound of the invention. Pharmaceutically acceptable salts can be derived, for example, from mineral acids (hydrochloric acid, hydrobromic acid, phosphoric acid, and the like), organic acids (acetic acid, propionic acid, glutamic acid, citric acid and the like), and quaternary ammonium ions. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The neutral form of a compound may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

As used herein, the term "pharmaceutical composition" refers to a product comprising a compound of the invention, an excipient as defined herein, and other optional ingredients in specified amounts, as well as any product which results directly or indirectly from combination of the specified ingredients in the specified amounts.

As used herein, the term "excipient" refers to a substance that aids the administration of an active agent to a subject. Pharmaceutical excipients useful in the present invention include, but are not limited to, binders, fillers, disintegrants, lubricants, coatings, sweeteners, flavors and colors. One of skill in the art will recognize that other excipients can be useful in the present invention.

As used herein, the terms "treat," "treating" and "treatment" refer to any indicia of success in the treatment or amelioration of a pathology, injury, condition, or symptom related to hypertrophic cardiomyopathy, including any objective or subjective parameter such as abatement; remission; diminishing of symptoms; making the pathology, injury, condition, or symptom more tolerable to the patient; decreasing the frequency or duration of the pathology, injury, condition, or symptom; or, in some situations, preventing the onset of the pathology, injury, condition, or symptom. Treatment or amelioration can be based on any objective or subjective parameter; including, e.g., the result of a physical examination.

III. Compounds

In one aspect, provided herein are compounds having the formula:

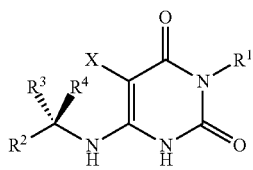

or pharmaceutically acceptable salts thereof. In these compounds, $R^1$ is a member selected from $C_1$-$C_8$ alkyl, $C_3$-$C_8$ cycloalkyl, $C_3$-$C_8$ cycloalkyl-$C_1$-$C_3$ alkyl, 4- to 7-membered heterocycloalkyl, 4- to 7-membered heterocycloalkyl-$C_1$-$C_3$ alkyl, phenyl, phenyl-$C_1$-$C_3$ alkyl, 5- to 6-membered heteroaryl and 5- to 6-membered heteroaryl-$C_1$-$C_3$ alkyl, wherein each $R^1$ is optionally substituted with from 1-3 $R^a$; $R^2$ is a member selected from $C_3$-$C_8$ cycloalkyl, $C_3$-$C_8$ cycloalkyl-$C_1$-$C_3$ alkyl, 4- to 7-membered heterocycloalkyl, and 4- to 7-membered heterocycloalkyl-$C_1$-$C_3$ alkyl, wherein each $R^2$ is optionally substituted with from 1-5 $R^b$; $R^3$ is a member selected from H, $C_1$-$C_4$ alkyl, $C_3$-$C_4$ cycloalkyl, and 4- to 7-membered heterocycloalkyl wherein each $R^3$ is optionally substituted with from 1-2 $R^c$; $R^4$ is a member selected from H and $C_1$-$C_4$ alkyl; or optionally, $R^3$ and $R^4$ are combined with the carbon atom to which each is attached, to form a 3- or 4-membered cycloalkyl or heterocycloalkyl ring; X is a member selected from H and F; each $R^a$ is independently selected from halo, CN, hydroxyl, $C_1$-$C_4$ alkyl, $C_1$-$C_4$ haloalkyl, $C_1$-$C_4$ alkoxy, —$COR^{a1}$, —$CO_2R^{a1}$, —$SO_2R^{a1}$, —$SO_2NR^{a1}R^{a2}$, and —$CONR^{a1}R^{a2}$, wherein each $R^{a1}$ and $R^{a2}$ is independently selected from H and $C_1$-$C_4$ alkyl or optionally $R^{a1}$ and $R^{a2}$ when attached to a nitrogen atom are combined to form a 4- to 6-membered ring; each $R^b$ is independently selected from halo, CN, hydroxyl, $C_1$-$C_4$ alkyl, $C_1$-$C_4$ haloalkyl, $C_1$-$C_4$ alkoxy, —$COR^{b1}$, —$CO_2R^{b1}$, $SO_2R^{b1}$, —$SO_2NR^{b1}R^{b2}$, and —$CONR^{b1}R^{b2}$, wherein each $R^{b1}$ and $R^{b2}$ is independently selected from H and $C_1$-$C_4$ alkyl or optionally $R^{b1}$ and $R^{b2}$ when attached to a nitrogen atom are combined to form a 4- to 6-membered ring; and each $R^c$ is independently selected from halo, hydroxyl and $C_1$-$C_2$ alkoxy.

In some embodiments, $R^1$ is $C_1$-$C_8$ alkyl, $C_3$-$C_8$ cycloalkyl, a 4- to 7-membered heterocycloalkyl, phenyl, or a 5- to 6-membered heteroaryl, wherein each $R^1$ is optionally substituted with from 1-3 $R^a$. $R^2$ is $C_3$-$C_8$ cycloalkyl, $C_3$-$C_8$ cycloalkyl $C_1$-$C_3$ alkyl, or a 4- to 7-membered heterocycloalkyl, wherein each $R^2$ is optionally substituted with from 1-5 $R^b$. $R^3$ is H, $C_1$-$C_4$ alkyl, $C_3$-$C_4$ cycloalkyl, or a 4- to 7-membered heterocycloalkyl wherein each $R^3$ is optionally substituted with from 1-2 $R^c$. $R^4$ can be H or $C_1$-$C_4$ alkyl. Optionally, $R^3$ and $R^4$ can be combined with the carbon atom to which each is attached to form a 3- or 4-membered cycloalkyl or heterocycloalkyl ring. In some embodiments, at least one of $R^3$ and $R^4$ is other than H. X can be H or F. Each $R^a$ is independently a halo, CN, $C_1$-$C_4$ alkyl, $C_1$-$C_4$ alkoxy, —$COR^{a1}$, —$CO_2R^{a1}$, —$SO_2R^{a1}$, —$SO_2NR^{a1}R^2$ or —$CONR^{a1}R^{a2}$, wherein each $R^{a1}$ and $R^{a2}$ is independently H or $C_1$-$C_4$ alkyl. Optionally, $R^{a1}$ and $R^{a2}$ when attached to a nitrogen atom are combined to form a 4- to 6-membered ring. Each $R^b$ is independently a halo, CN, $C_1$-$C_4$ alkyl, $C_1$-$C_4$ alkoxy, —$COR^{b1}$, —$CO_2R^{b1}$, —$SO_2R^{b1}$, $SO_2NR^{b1}R^{b2}$, or —$CONR^{b1}R^{b2}$, wherein each $R^{b1}$ and $R^{b2}$ is independently H or $C_1$-$C_4$ alkyl. Optionally, $R^{b1}$ and $R^{b2}$ when attached to a nitrogen atom are combined to form a 4- to 6-membered ring. Each $R^c$ is independently a halo or $C_1$-$C_2$ alkoxy.

In some embodiments, X is H.

In some embodiments, $R^1$ is $C_3$-$C_4$ alkyl, $C_3$-$C_5$ cycloalkyl, or 4- to 6-membered heterocycloalkyl, wherein each $R^1$ is optionally substituted with from 1-2 $R^a$.

In some embodiments, $R^1$ is phenyl or 5- to 6-membered heteroaryl, wherein each $R^1$ is optionally substituted with from 1-3 $R^a$.

In some embodiments, $R^1$ is $C_3$-$C_4$ alkyl, $C_3$-$C_5$ cycloalkyl, or 4- to 6-membered heterocycloalkyl.

In some embodiments, $R^1$ is a 4- to 6-membered heterocycloalkyl, optionally substituted with from 1-2 $R^a$ is $C_1$-$C_4$ alkyl, $C_1$-$C_4$ alkoxy, —$COR^{a1}$, —$CO_2R^{a1}$, —$SO_2R^{a1}$, —$SO_2NR^{a1}R^{a2}$, and —$CONR^{a1}R^{a2}$, wherein each $R^{a1}$ and $R^{a2}$ is independently a H and $C_1$-$C_4$ alkyl.

In some embodiments, $R^1$ is cyclobutyl, isopropyl, isobutyl, 1-methoxypropan-2-yl, cyclopentyl, cyclohexyl, 4-tetrahydropyranyl, 1-(methylsulfonyl)piperidin-4-yl, 1-(methoxycarbonyl)piperidin-4-yl, 4,4-difluorocyclohexyl, phenyl, 2-pyridyl, 3-pyridyl, 3-isoxazolyl, 5-isoxazolyl, or 1-methyl-3-pyrazolyl.

In some embodiments, $R^2$ is $C_4$-$C_6$ cycloalkyl, $C_4$-$C_6$ cycloalkyl $C_1$-$C_2$ alkyl, or a 5- to 6-membered heterocycloalkyl, wherein each $R^2$ is optionally substituted with from 1-2 $R^b$.

In some embodiments, $R^2$ is cyclohexyl, 4,4-difluorocyclohexyl, or (4,4-difluorocyclohexyl)methyl.

In some embodiments, $R^2$ is a 4- to 7-membered heterocycloalkyl, which is optionally substituted with from 1-2 $R^b$.

In some embodiments, $R^3$ is $C_1$-$C_4$ alkyl, $C_1$-$C_4$ alkoxyalkyl, or $C_3$-$C_4$ cycloalkyl.

In some embodiments, $R^3$ is methyl, ethyl, propyl, cyclopropyl, cyclobutyl and 2-methoxymethyl.

In some embodiments, $R^3$ is methyl.

In some embodiments, $R^4$ is H, methyl or ethyl.

In some embodiments, $R^3$ is methyl and $R^4$ is H.

The compounds or their pharmaceutically acceptable salts provided herein can have any combination of the $R^1$, $R^2$, $R^3$, $R^4$, $R^a$, $R^{a1}$, $R^{a2}$, $R^b$, $R^{b1}$, $R^{b2}$, $R^c$, and X groups recited above.

Selected embodiments recited for $R^2$, for example, is combined with any of the selected embodiments recited for $R^1$ which, in turn, is combined with any of the selected embodiments recited for $R^3$ or $R^4$.

In some embodiments, for example, $R^1$ is $C_3$-$C_8$ alkyl; $R^3$ is $C_3$-$C_4$ cycloalkyl or a 4- to 7-membered heterocycloalkyl; and $R^2$ is $C_4$-$C_6$ cycloalkyl or $C_4$-$C_6$ cycloalkyl $C_1$-$C_2$ alkyl. In other embodiments, $R^1$ is a 4- to 7-membered heterocycloalkyl or a 5- to 6-membered heteroaryl which is optionally substituted with $C_1$-$C_4$ alkyl, —$CO_2R^{a1}$, or —$SO_2R^{a1}$; $R^3$ is $C_3$-$C_4$ cycloalkyl or a 4- to 7-membered heterocycloalkyl; and $R^2$ is $C_4$-$C_6$ cycloalkyl or $C_4$-$C_6$ cycloalkyl $C_1$-$C_2$ alkyl. In other embodiments, $R^1$ is $C_3$-$C_8$ cycloalkyl or phenyl, $R^3$ is $C_3$-$C_4$ cycloalkyl or a 4- to 7-membered heterocycloalkyl; and $R^2$ is $C_4$-$C_6$ cycloalkyl or $C_4$-$C_6$ cycloalkyl $C_1$-$C_2$ alkyl. Each $R^2$ is optionally substituted with from 1-2 $R^b$.

In some embodiments, $R^1$ is $C_3$-$C_8$ alkyl; $R^3$ is $C_1$-$C_4$ alkyl; and $R^2$ is $C_4$-$C_6$ cycloalkyl or $C_4$-$C_6$ cycloalkyl $C_1$-$C_2$ alkyl. In other embodiments, $R^1$ is a 4- to 7-membered heterocycloalkyl or a 5- to 6-membered heteroaryl which is optionally substituted with $C_1$-$C_4$ alkyl, —$CO_2R^{a1}$, or —$SO_2R^{a1}$; $R^3$ is $C_1$-$C_4$ alkyl; and $R^2$ is $C_4$-$C_6$ cycloalkyl or $C_4$-$C_6$ cycloalkyl $C_1$-$C_2$ alkyl. In other embodiments, $R^1$ is $C_3$-$C_8$ cycloalkyl or phenyl; $R^3$ is $C_1$-$C_4$ alkyl; and $R^2$ is $C_4$-$C_6$ cycloalkyl or $C_4$-$C_6$ cycloalkyl $C_1$-$C_2$ alkyl. Each $R^2$ is optionally substituted with from 1-2 $R^b$.

In some embodiments, for example, $R^1$ is $C_3$-$C_8$ alkyl; $R^3$ is $C_3$-$C_4$ cycloalkyl or a 4- to 7-membered heterocycloalkyl; and $R^2$ is a 4- to 7-membered heterocycloalkyl. In other embodiments, $R^1$ is a 4- to 7-membered heterocycloalkyl or a 5- to 6-membered heteroaryl which is optionally substituted with $C_1$-$C_4$ alkyl, —$CO_2R^{a1}$, or —$SO_2R^{a1}$; $R^3$ is $C_3$-$C_4$ cycloalkyl or a 4- to 7-membered heterocycloalkyl; and $R^2$ is a 4- to 7-membered heterocycloalkyl. In other embodiments, $R^1$ is $C_3$-$C_8$ cycloalkyl or phenyl, $R^3$ is $C_3$-$C_4$ cycloalkyl or a 4- to 7-membered heterocycloalkyl; and $R^2$ is a 4- to 7-membered heterocycloalkyl. Each $R^2$ is optionally substituted with from 1-2 $R^b$.

In some embodiments, $R^1$ is $C_3$-$C_8$ alkyl; $R^3$ is $C_1$-$C_4$ alkyl; and $R^2$ is a 4- to 7-membered heterocycloalkyl. In other embodiments, $R^1$ is a 4- to 7-membered heterocycloalkyl or a 5- to 6-membered heteroaryl which is optionally substituted with $C_1$-$C_4$ alkyl, —$CO_2R^{a1}$ or —$SO_2R^{a1}$; $R^3$ is $C_1$-$C_4$ alkyl; and $R^2$ is a 4- to 7-membered heterocycloalkyl. In other embodiments, $R^1$ is $C_3$-$C_8$ cycloalkyl or phenyl; $R^3$ is $C_1$-$C_4$ alkyl; and $R^2$ is a 4- to 7-membered heterocycloalkyl. Each $R^2$ is optionally substituted with from 1-2 $R^b$.

In certain selected embodiments $R^2$ is cyclohexyl, 4,4-difluorocyclohexyl, or (4,4-difluorocyclohexyl)methyl.

In some embodiments, $R^1$ is isopropyl; $R^2$ is $C_4$-$C_6$ cycloalkyl, $C_4$-$C_6$ cycloalkyl $C_1$-$C_2$ alkyl, or a 5- to 6-membered heterocycloalkyl, wherein each $R^2$ is optionally substituted with from 1-2 $R^b$; $R^3$ is methyl; and $R^4$ is H.

In some embodiments, $R^1$ is phenyl or a 5- to 6-membered heteroaryl, wherein each $R^1$ is optionally substituted with from 1-3 $R^a$; $R^2$ is $C_4$-$C_6$ cycloalkyl, $C_4$-$C_6$ cycloalkyl-$C_1$-$C_2$ alkyl, or a 5- to 6-membered heterocycloalkyl, wherein each $R^2$ is optionally substituted with from 1-2 $R^b$; $R^3$ is methyl; and $R^4$ is H.

In one group of selected embodiments, X is H (including any of the embodiments set forth above). In other embodiments, X is F in any of the embodiments set forth above.

In some embodiments, the compound is selected from:
6-((cyclohexylmethyl)amino)-3-isopropylpyrimidine-2,4 (1H,3H)-dione;
6-((cyclopentylmethyl)amino)-3-isopropylpyrimidine-2,4 (1H,3H)-dione;
(S)-6-((1-(4,4-difluorocyclohexyl)propan-2-yl)amino)-3-isopropylpyrimidine-2,4(1H,3H)-dione;
(S)-6-((1-(4,4-difluorocyclohexyl)ethyl)amino)-3-(tetrahydro-2H-pyran-4-yl)pyrimidine-2,4(1H,3H)-dione;
(S)-6-((1-(4,4-difluorocyclohexyl)ethyl)amino)-5-fluoro-3-isopropylpyrimidine-2,4(1H,3H)-dione;
(S)-6-((1-cyclohexylethyl)amino)-3-isopropylpyrimidine-2,4(1H,3H)-dione;
6-((cyclobutylmethyl)amino)-3-isopropylpyrimidine-2,4 (1H,3H)-dione;
6-((cycloheptylmethyl)amino)-3-isopropylpyrimidine-2,4 (1H,3H)-dione;
(S)-6-((1-(4,4-difluorocyclohexyl)ethyl)amino)-3-isopropylpyrimidine-2,4(1H,3H)-dione;
(S)-6-((1-(3,3-difluorocyclobutyl)propan-2-yl)amino)-3-isopropylpyrimidine-2,4(1H,3H)-dione;
(S)-6-((1-(4,4-difluorocyclohexyl)propan-2-yl)amino)-3-(3,5-difluorophenyl)pyrimidine-2,4(1H,3H)-dione;
(S)-6-((1-(3,3-difluorocyclobutyl)propan-2-yl)amino)-3-(3,5-difluorophenyl)pyrimidine-2,4(1H,3H)-dione;
3-isopropyl-6-((2-(tetrahydro-2H-pyran-4-yl)ethyl)amino) pyrimidine-2,4(1H,3H)-dione;
(S)-3-isopropyl-6-((1-(tetrahydro-2H-pyran-4-yl)propan-2-yl)amino)pyrimidine-2,4(1H,3H)-dione; and
(S)-6-((1-cyclohexylethyl)amino)-3-(1-(methylsulfonyl)piperidin-4-yl)pyrimidine-2,4(1H,3H)-dione, or pharmaceutically acceptable salts thereof In some embodiments, the compound is selected from

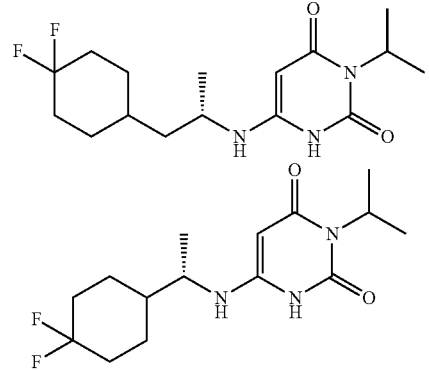

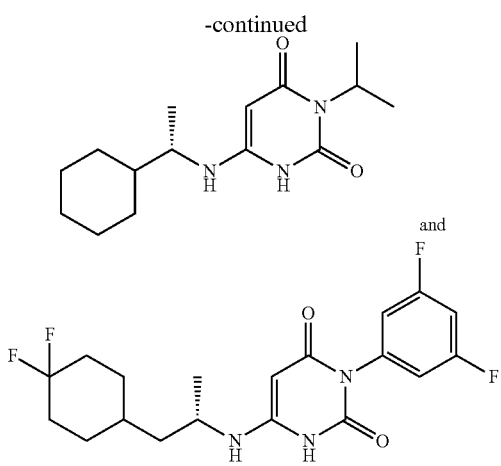

or pharmaceutically acceptable salts thereof

The compounds of formula (I) can be prepared via any suitable method. Compounds can be prepared, for example, by the route outlined in FIG. 1. As shown in FIG. 1A, a pyrimidine trione v can be synthesized via condensation of a urea iii with a malonate iv. The urea iii can be prepared via reaction of an amine i with an appropriate cyanate ii. The pyrimidine trione v is derivatized with a suitable leaving group (Lg) to provide intermediate vi. The leaving group can be, but is not limited to, a halogen such as a chloride or iodide. A halogenated intermediate vi can be prepared from pyrimidine triones by methods such as those described by Brown (*The Chemistry of Heterocyclic Compounds, The Pyrimidines*, John Wiley & Sons, 2009). Intermediates vi can be converted to compounds of formula I via reaction with amines vii. Certain chiral amines can be prepared from a ketone or aldehyde ix as shown in FIG. 1B; a sulfinyl imine xii derived from the ketone or aldehyde can be reacted with a Gringard reagent xiii to provide a chiral amine vii. One of skill in the art will appreciate that the compounds of invention can be prepared using other synthetic methods, including transformations as described in, for example, LaRock (*Comprehensive Organic Transformations: A Guide to Functional Group Preparations*, Wiley, 1999).

IV. Compositions

In another aspect, provided herein is a pharmaceutical composition containing a compound of formula I or a pharmaceutically acceptable salt thereof and a pharmaceutically acceptable excipient. The compositions are useful for treating hypertrophic cardiomyopathy in humans and other subjects.

The pharmaceutical compositions for the administration of the compounds or their pharmaceutically acceptable salts provided herein may conveniently be presented in unit dosage form and may be prepared by any of the methods known in the art of pharmacy and drug delivery. All methods include the step of bringing the active ingredient into association with a carrier containing one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active agent is generally included in an amount sufficient to produce the desired effect upon myocardial contractility (i.e. to decrease the often supranormal systolic contractility in HCM) and to improve left ventricular relaxation in diastole. Such improved relaxation can alleviate symptoms in hypertrophic cardiomyopathy and other etiologies of diastolic dysfunction. It can also ameliorate the effects of diastolic dysfunction causing impairment of coronary blood flow, improving the latter as an adjunctive agent in angina pectoris and ischemic heart disease. It can also confer benefits on salutary left ventricular remodeling in HCM and other causes of left ventricular hypertrophy due to chronic volume or pressure overload from, e.g., valvular heart disease or systemic hypertension The pharmaceutical compositions containing the active ingredient may be in a form suitable for oral use, for example, as tablets, troches, lozenges, aqueous or oily suspensions, dispersible powders or granules, emulsions, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or *acacia*, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum *acacia*; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions provided herein may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum *acacia* or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds or their pharmaceutically acceptable salts provided herein may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds or their pharmaceutically acceptable salts provided herein are employed. As used herein, topical application is also meant to include the use of mouth washes and gargles.

The compounds of this invention may also be coupled to a carrier that is a suitable polymer for targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds or their pharmaceutically acceptable salts provided herein may be coupled to a carrier that is a biodegradable polymer useful in achieving controlled release of a drug, such as polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

V. Methods of Treating Cardiac Disorders

The mutations that lead to HCM cause significant perturbations in myosin mechanics. These mutations exert their effects via distinct mechanisms depending on their locations in the myosin gene. The well-studied HCM mutations, R403Q and R453C, are located in different sections of the motor domain and cause distinct mechanistic perturbations that lead to the common outcome of increased force production. Without wishing to be bound by any particular theory, it is believed that the compounds or their pharmaceutically acceptable salts provided herein can bind directly to the mutant sarcomeric proteins and correct for their aberrant function, either in cis (by affecting the same specific function) or in trans (by altering a complementary function). As such, they can provide therapeutic benefit for HCM patients by counteracting the hypercontractile and/or impaired relaxation associated with this disease.

Accordingly, the invention provides a method of treating hypertrophic cardiomyopathy (HCM) or a cardiac disorder having one or more pathophysiological features associated with HCM. The method includes administering to a subject in need thereof an effective amount of a compound provided herein.

The compounds of the invention or their pharmaceutically acceptable salts can alter the natural history of HCM and other diseases rather than merely palliating symptoms. The mechanisms conferring clinical benefit to HCM patients can extend to patients with other forms of heart disease sharing similar pathophysiology, with or without demonstrable genetic influence. For example, an effective treatment for HCM, by improving ventricular relaxation during diastole, can also be effective in a broader population characterized by diastolic dysfunction. The compounds of the invention or their pharmaceutically acceptable salts can specifically target the root causes of the conditions or act upon other downstream pathways. Accordingly, the compounds of the invention or their pharmaceutically acceptable salts can also confer benefit to patients suffering from diastolic heart failure with preserved ejection fraction, ischemic heart disease, angina pectoris, or restrictive cardiomyopathy. Compounds of the invention or their pharmaceutically acceptable salts can also promote salutary ventricular remodeling of left ventricular hypertrophy due to volume or pressure overload; e.g., chronic mitral regurgitation, chronic aortic stenosis, or chronic systemic hypertension; in conjunction with therapies aimed at correcting or alleviating the primary cause of volume or pressure overload (valve repair/replacement, effective antihypertensive therapy). By reducing left ventricular filling pressures the compounds could reduce the risk of pulmonary edema and respiratory failure. Reducing or eliminating functional mitral regurgitation and/or lowering left atrial pressures may reduce the risk of paroxysmal or permanent atrial fibrillation, and with it reduce the attendant risk of arterial thromboembolic complications including but not limited to cerebral arterial embolic stroke. Reducing or eliminating either dynamic and/or static left ventricular outflow obstruction may reduce the likelihood of requiring septal reduction therapy, either surgical or percutaneous, with their attendant risks of short and long term complications. The compounds or their pharmaceutically acceptable salts may reduce the severity of the chronic ischemic state associated with HCM and thereby reduce the risk of Sudden Cardiac Death (S C D) or its equivalent in patients with implantable cardioverter-defibrillators (frequent and/or repeated ICD discharges) and/or the need for potentially toxic antiarrhythmic medications. The compounds or their pharmaceutically acceptable salts could be valuable in reducing or eliminating the need for concomitant medications with their attendant potential toxicities, drug-drug interactions, and/or side effects. The compounds or their pharmaceutically acceptable salts may reduce interstitial myocardial fibrosis and/or slow the progression, arrest, or reverse left ventricular hypertrophy.

Depending on the disease to be treated and the subject's condition, the compounds or their pharmaceutically acceptable salts provided herein may be administered by oral, parenteral (e.g., intramuscular, intraperitoneal, intravenous, ICV, intracisternal injection or infusion, subcutaneous injection, or implant), by implantation (e.g., as when the compound is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require improved ventricular relaxation during diastole, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Compounds and compositions provided herein may be used in combination with other drugs that are used in the treatment, prevention, suppression or amelioration of the diseases or conditions for which compounds and compositions provided herein are useful. Such other drugs may be administered, by a route and in an amount commonly used therefor, contemporaneously or sequentially with a compound or composition provided herein. When a compound or composition provided herein is used contemporaneously with one or more other drugs, a pharmaceutical composition containing such other drugs in addition to the compound or composition provided herein is preferred. Accordingly, the pharmaceutical compositions provided herein include those that also contain one or more other active ingredients or therapeutic agents, in addition to a compound or composition provided herein. Suitable additional active agents include, for example: therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The weight ratio of the compound provided herein to the second active ingredient may be varied and will depend upon the effective dose of each ingredient. Generally, an effective dose of each will be used.

VI. Examples aq: aqueous
$BBr_3$: boron tribromide
$CH_2Cl_2$: dichloromethane
$CH_3CN$: acetonitrile
$CH_3OH$: methanol
DIAD: diisopropyl azodicarboxylate
DIEA: diisopropyl ethylamine
DMF: dimethyl formamide
DMSO: dimethyl sulfoxide
equiv.: equivalents
$Et_3N$: triethylamine
$Et_2O$: diethyl ether
EtOH: ethanol
h: hour(s)
HCl: hydrogen chloride
$H_2O$: water
$K_2CO_3$: potassium carbonate
$KHSO_4$: potassium bisulfate
KNCO: potassium isocyanate
$MgSO_4$: magnesium sulfate
mL: milliliter
MW: microwave (reaction done in microwave reactor)
NaCl: sodium chloride
NaH: sodium hydride
$NaHCO_3$: sodium bicarbonate NaOEt: sodium ethoxide
NaOH: sodium hydroxide
NaOMe: sodium methoxide
$Na_2SO_4$: sodium sulfate
$NH_4Cl$: ammonium chloride
NMP: n-methyl pyrrolidinone
pH: $-\log [H^+]$
$POCl_3$: phosphoryl trichloride
PPTS: pyridinium p-toluenesulfonate
RP-HPLC: reversed phase high pressure liquid chromatography
RT: room temperature
TEBAC: triethylbenzylammonium chloride
TFA: trifluoroacetic acid
THF: tetrahydrofuran Example 1

Preparation of 6-((cyclohexylmethyl)amino)-3-isopropylpyrimidine-2,4(1H,3H)-dione

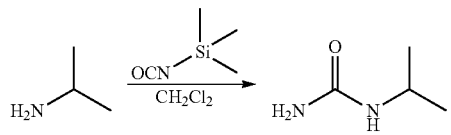

Compound 1.1. Isopropylurea

To a stirred solution of isopropylamine (15.3 g, 258.84 mmol, 1.00 equiv) in $CH_2Cl_2$ (200 mL) under argon at 0° C. was added dropwise trimethylsilyl isocyanate (30 g, 260.40 mmol, 1.00 equiv). The resulting mixture was allowed to reach ambient temperature and stirred overnight. After cooling to 0° C., $CH_3OH$ (100 mL) was added dropwise. The resulting solution was stirred 2 h at room temperature and then concentrated under reduced pressure. The crude residue was recrystallized from $CH_3OH:Et_2O$ (1:20) to yield 15.4 g (58%) of a white solid.

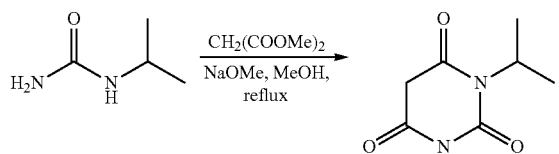

Compound 1.2. 1-Isopropyl barbituric acid

To a stirred solution of 1.1 (14.4 g, 0.141 mol, 1.00 equiv) in $CH_3OH$ (500 mL) were added dimethyl malonate (19.55 g, 0.148 mol, 1.05 equiv) and sodium methoxide (18.9 g, 0.35 mol, 2.50 equiv). The resulting mixture was stirred overnight at 65° C. After cooling to ambient temperature and then to 0° C., the pH was carefully adjusted to 3 using aqueous concentrated HCl. The resulting mixture was concentrated under reduced pressure. The residue was taken up in EtOH (200 mL) and filtered. The filtrate was concentrated under reduced pressure and the residue was purified using silica gel column chromatography using $CH_2Cl_2/CH_3OH$ (20:1) as eluent to yield 16.8 g (50%) of a white solid. $^1$H-NMR (300 MHz, DMSO-$d_6$): δ ppm 11.19 (s, 1H), 4.83 (m, 1H), 3.58 (s, 2H), 1.32 (d, J=6.0 Hz, 6H).

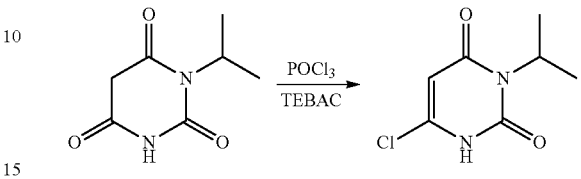

Compound 1.3.
6-chloro-3-isopropylpyrimidine-2,4(1H,3H)-dione

To a 100-mL round-bottom flask containing 1.2 (11.4 g, 66.99 mmol, 1.00 equiv) under argon were added triethylbenzylammonium chloride (21.3 g, 93.51 mmol, 1.40 equiv) and $POCl_3$ (30 mL). The resulting mixture was stirred overnight at 50° C. After cooling to room temperature, the mixture was concentrated under reduced pressure. The residue was dissolved in $CH_2Cl_2$ (150 mL) followed by slow addition of $H_2O$ (100 mL). The phases were extracted and separated. The organic layer was washed with $H_2O$, dried with anhydrous $Na_2SO_4$, and concentrated under reduced pressure. The crude residue was purified using silica gel column chromatography using EtOAc/petroleum ether (1:1) as eluent to yield 5.12 g (40%) of the title compound as a light yellow solid. $^1$H-NMR (300 MHz, DMSO-$d_6$): δ ppm 12.22 (s, 1H), 5.88 (s, 1H), 4.95 (m, 1H), 1.34 (d, J=6.0 Hz, 6H).

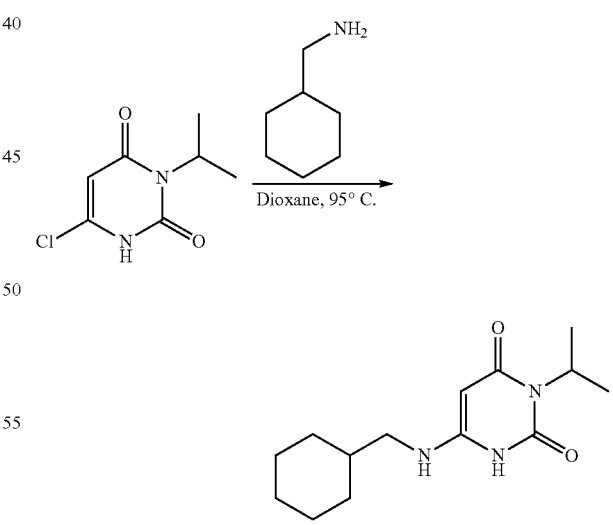

Compound 1. 6-((cyclohexylmethyl)amino)-3-isopropylpyrimidine-2,4(1H,3H)-dione

To a stirred solution of 1.3 (40 mg, 0.21 mmol) in dioxane (1 mL) was added cyclohexylmethanamine (57 mg, 0.51 mmol). The reaction mixture was plunged into a preheated 95° C. oil bath and was stirred for 72 h. The reaction mixture was cooled to room temperature and a precipitate formed. The precipitate was isolated by filtration and was washed with CH$_2$Cl$_2$ (2×5 mL). The solid was dried under high vacuum for 2 h to provide 45 mg (81%) of the title compound as a white solid. LC/MS: m/z (ES+) 266 (M+H)$^+$. $^1$H-NMR (400 MHz, CDCl$_3$): δ ppm 10.31 (br s, 1H), 5.36 (br s, 1H), 5.14 (m, 1H), 4.75 (s, 1H), 2.79-2.92 (m, 3H), 1.65-1.89 (m, 4H), 1.41 (d, J=7.04 Hz, 6H), 1.12-1.34 (m, 3H), 0.85-1.10 (m, 3H).

Example 2

Preparation of 6-((Cyclopentylmethyl)amino)-3-isopropylpyrimidine-2,4(1H,3H)-dione

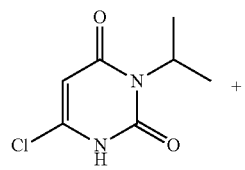

+

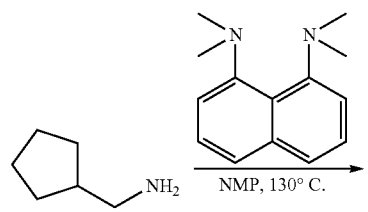

Compound 2. 6-((Cyclopentylmethyl)amino)-3-isopropylpyrimidine-2,4(1H,3H)-dione

A solution of 1.3, (50 mg, 0.27 mmol), cyclopentylmethylamine (78 mg, 0.79 mmol) and proton sponge (80 mg, 0.37 mmol) in NMP (0.5 mL) was stirred at 130° C. for 5 h. After cooling to room temperature, the mixture was purified by RP-HPLC: reversed phase high pressure liquid chromatography (Shimadzu, Prominence LC-20AP system equipped with a Phenomenex Gemini-NX C18 column), eluting with 20-90% CH$_3$CN in H$_2$O (both containing 0.1% TFA) to give crude sample (31 mg), which was further purified by flash column chromatography (silica gel, eluted with 0-5% CH$_3$OH in CH$_2$Cl$_2$) to give 5 mg of the title compound (7%). LC/MS: m/z (ES+) 252 (M+H)$^+$. $^1$H-NMR (400 MHz, CDCl$_3$) δ ppm 10.58 (br s, 1H), 5.18-5.11 (m, 1H), 4.93 (app t, J=4.0 Hz, 1H), 4.83 (s, 1H), 3.00 (m, 2H), 2.17-2.10 (m, 1H), 1.84-1.76 (m, 2H), 1.68-1.53 (m, 4H), 1.43 (d, J=4.0 Hz, 6H), 1.28-1.18 (m, 2H).

Example 3

Preparation of (S)-6-((1-(4,4-Difluorocyclohexyl)propan-2-yl)amino)-3-isopropylpyrimidine-2,4(1H,3H)-dione

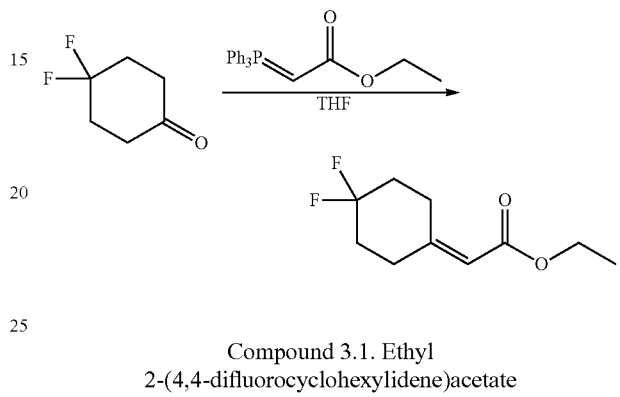

Compound 3.1. Ethyl 2-(4,4-difluorocyclohexylidene)acetate

A solution of 4,4-difluorocyclohexan-1-one (1.0 g, 7.46 mmol, 1.00 equiv) and (carbethoxymethylene)triphenylphosphorane (3.9 g, 24.05 mmol, 1.50 equiv) in THF (20 mL) was stirred under argon overnight at 65° C. After cooling to ambient temperature, the mixture was concentrated under reduced pressure and the crude residue was purified using flash column chromatography (silica gel, EtOAc/petroleum ether (1:10)) to yield 1.5 g (97%) of a colorless oil. $^1$H-NMR (400 MHz, CDCl$_3$): δ ppm 5.75 (s, 1H), 4.18 (m, 2H), 3.06 (t, J=6.8 Hz, 2H), 2.34 (t, J=6.8 Hz, 2H), 2.11-1.99 (m, 4H), 1.33-1.26 (m, 3H).

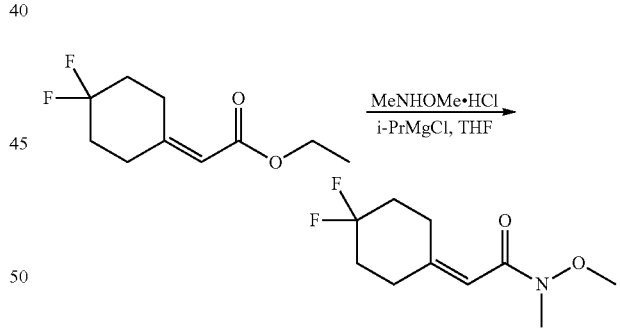

Compound 3.2. 2-(4,4-difluorocyclohexylidene)-N-methoxy-N-methylacetamide

To a mixture of 3.1 (1.7 g, 8.32 mmol, 1.00 equiv) and methoxy(methyl)amine hydrochloride (1.22 g, 12.5 mmol, 1.50 equiv) in THF (40 mL) at −15° C. under argon was added dropwise isopropylmagnesium chloride (13 mL, 25.0 mmol, 1.9 M in THF). The solution was allowed to reach room temperature and was stirred for 1 h. The reaction mixture was cooled to 10° C. and was carefully quenched by slow addition of aqueous saturated NH$_4$Cl (30 mL). The resulting mixture was extracted with EtOAc (2×50 mL). The combined organic layers were washed with H$_2$O (50 mL), dried with anhydrous Na$_2$SO$_4$, and concentrated under reduced pressure. The crude residue was purified using flash column chromatography (silica gel, EtOAc/petroleum ether (1:1)) to yield 1.4 g (73%) of the title compound as a yellow oil. $^1$H-NMR (400 MHz, CDCl$_3$): δ ppm 6.19 (br s, 1H), 3.82-3.54 (m, 3H), 3.36-3.14 (m, 3H), 3.00 (m, 2H), 2.45 (m, 2H), 2.05 (m, 4H).

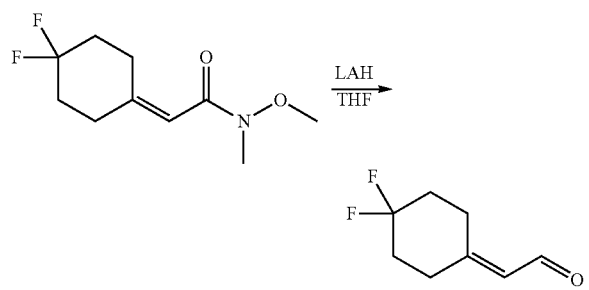

Compound 3.3.
2-(4,4-Difluorocyclohexylidene)acetaldehyde

To a solution of 3.2 (6.5 g, 29.7 mmol, 1.00 equiv) in THF (60 mL) at 0° C. under argon was carefully added lithium aluminum hydride (2.25 g, 59.21 mmol, 2.00 equiv) in several batches. The mixture was allowed to warm to room temperature and was stirred for an additional 1 h. The mixture was cooled to 10° C. and the reaction was carefully quenched by slow addition of aqueous saturated NH$_4$Cl (60 mL). The resulting mixture was extracted with EtOAc (3×200 mL). The combined organic layers were dried with anhydrous Na$_2$SO$_4$ and concentrated under reduced pressure to yield 5.7 g (98%) of a yellow oil which was used directly in the next step without further purification.

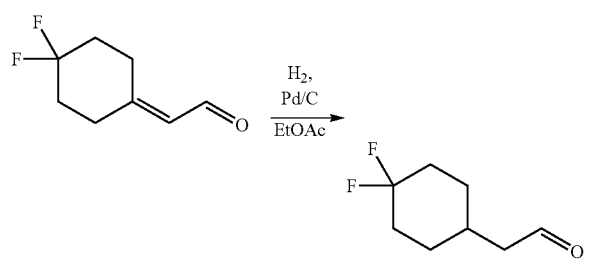

Compound 3.4.
2-(4,4-Difluorocyclohexyl)acetaldehyde

A 50-mL round-bottom flask containing a solution of 3.3 (5.7 g, 35.6 mmol, 1.00 equiv) in EtOAc (50 mL) was purged with nitrogen. To the flask was then added palladium on carbon (100 mg, 10%, ~60% H$_2$O). After purging the flask further with nitrogen, the atmosphere was charged with hydrogen and the mixture was stirred at ambient temperature. After 20 minutes, the flask was purged with nitrogen, the solids were removed by filtration, and the filtrate was concentrated under reduced pressure to yield 4.0 g (60%) of a yellow oil which was used directly in the next step without further purification.

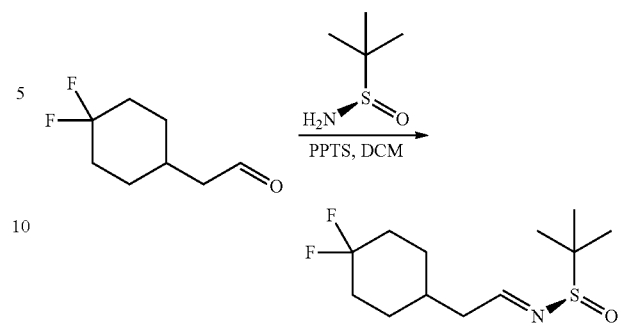

Compound 3.5. (R)—N-(2-(4,4-Difluorocyclohexyl)ethylidene)-2-methylpropane-2-sulfinamide A mixture of 3.4 (4.0 g, 24.7 mmol, 1.00 equiv), (R)-(+)-2-methyl-2-propanesulfinamide (3.0 g, 24.8 mmol, 1.00 equiv), and PPTS (0.27 g, 0.05 equiv) in CH$_2$Cl$_2$ (80 mL) was stirred at ambient temperature overnight. The mixture was then concentrated under reduced pressure and the crude residue was purified using flash column chromatography (silica gel, EtOAc/petroleum ether (1:4)) to yield 4.1 g (58%) of a yellow oil.

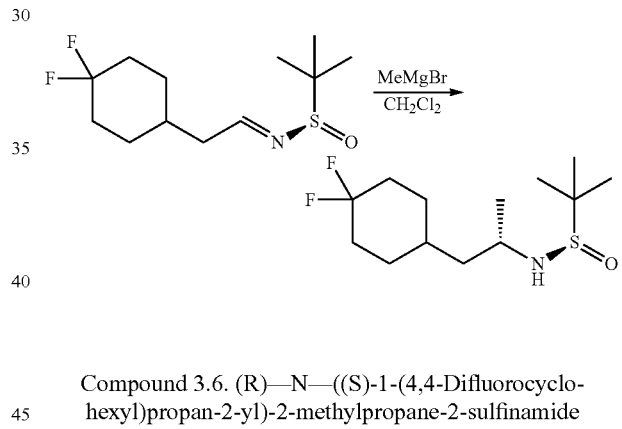

Compound 3.6. (R)—N—((S)-1-(4,4-Difluorocyclohexyl)propan-2-yl)-2-methylpropane-2-sulfinamide To a solution of 3.5 (4.1 g, 15.5 mmol, 1.00 equiv) in CH$_2$Cl$_2$ (80 mL) under argon at −48° C. was added dropwise methylmagnesium bromide (15.5 mL, 46.5 mmol, 3.0 M in THF, 3.0 equiv). The resulting mixture was stirred at −48° C. for 6 h and then at room temperature overnight. The reaction was then cooled to −50° C. and carefully quenched by the addition of aqueous saturated NH$_4$Cl (100 mL). The mixture was then filtered and the filtrate was extracted with EtOAc (3×100 mL). The combined organic phases were dried with anhydrous Na$_2$SO$_4$ and concentrated under reduced pressure to yield 3.2 g (63%) of a yellow oil which was used directly in the next step without further purification.

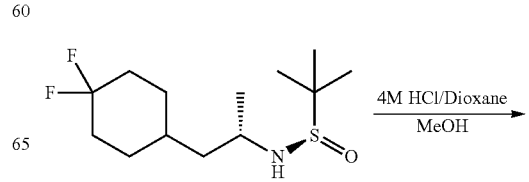

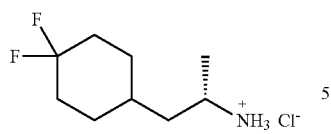

Compound 3.7.
(S)-1-(4,4-Difluorocyclohexyl)propan-2-amine hydrochloride

A solution of 3.6 (3.2 g, 11.4 mmol) in 4M HCl in 1,4-dioxane (30 mL) was stirred under argon for 2 h at room temperature. The resulting mixture was then concentrated under reduced pressure. The residue was dissolved with CH₃OH (3 mL) and then diluted Et₂O (300 mL). The resulting precipitate was collected by filtration to yield 932 mg (37%) of a white solid. LC/MS: m/z (ES+) 219 (M+H)⁺. ¹H-NMR (400 MHz, D₂O): δ ppm 3.37 (m, 1H), 2.02 (m, 2H), 1.73 (m, 4H), 1.47 (m, 3H), 1.14 (m, 5H).

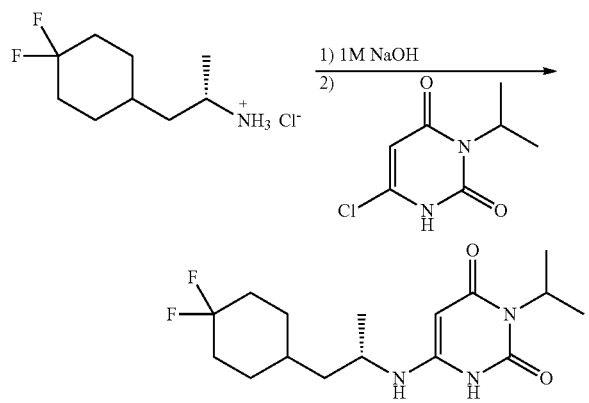

Compound 3. (S)-6-((1-(4,4-Difluorocyclohexyl)propan-2-yl)amino)-3-isopropylpyrimidine-2,4(1H,3H)-dione A mixture of 3.7 (100 mg, 0.56 mmol, 2.00 equiv) and aqueous NaOH (10 mL, 10 mmol) was stirred at ambient temperature. After 1 h, the mixture was extracted with EtOAc (5×10 mL). The combined organic layers were dried with anhydrous Na₂SO₄ and concentrated under reduced pressure. To the residue was added 1.3 (50 mg, 0.28 mmol, 1.0 equiv) and the reaction mixture was purged with argon and heated at 100° C. overnight. After cooling to room temperature, the crude product was purified by preparative RP-HPLC (Waters) using the following conditions: column, XBridge Prep C18 OBD 5 um, 19*150 mm; mobile phase, H₂O with 0.01M ammonium bicarbonate and CH₃CN (15% CH₃CN up to 75% in 10 min); detector, UV 254 & 220 nm. The fractions containing pure compound were combined and lyophilized to yield 36.3 mg (19%) of a white solid. LC/MS: m/z (ES+) 330 (M+H)⁺. ¹H-NMR (400 MHz, DMSO-d₆): δ ppm 9.76 (br s, 1H), 5.88 (d, J=8.0 Hz, 1H), 4.97 (m, 1H), 4.55 (s, 1H), 3.48 (m, 1H), 2.07-1.92 (m, 2H), 1.89-1.67 (m, 4H), 1.50-1.36 (m, 3H), 1.32 (d, J=7.0 Hz, 6H), 1.20-1.10 (m, 2H), 1.09 (d, J=6.3 Hz, 3H).

Example 4

Preparation of (S)-6-((1-(4,4-difluorocyclohexyl)ethyl)amino)-3-(tetrahydro-2H-pyran-4-yl)pyrimidine-2,4(1H,3H)-dione

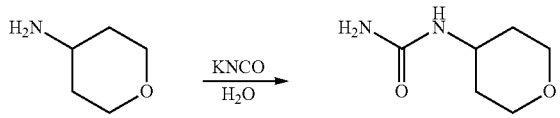

Compound 4.1. 1-(tetrahydro-2H-pyran-4-yl)urea

A mixture of tetrahydro-2H-pyran-4-amine (5.0 g, 49.4 mmol, 1 equiv.) and potassium isocyanate (4.0 g, 49.5 mmol, 1.0 equiv.) was refluxed in H₂O (50 mL) overnight. The reaction was cooled to room temperature and excess NaCl was added to help saturate the aqueous layer. The precipitate was isolated by filtration to provide the desired product (1.28 g, 8.88 mmol). The aqueous layer was washed with EtOAc (3×15 mL) and then was concentrated and azeotroped with toluene (3×100 mL). The resulting solid was suspended in 1:4 MeOH:EtOAc (100 mL) and filtered a total of four times. The combined organics were concentrated under reduced pressure and combined with the isolated precipitate to provide 5.01 g (70%) of the title compound. LC/MS: m/z (ES+) 145 (M+H)⁺. ¹H NMR (400 MHz, DMSO-d₆): δ ppm 6.14 (d, J=7.5 Hz, 1H), 5.47 (s, 2H), 3.85 (dt, J=11.6, 3.6 Hz, 2H), 3.65-3.52 (m, 1H), 3.38 (td, J=11.4, 2.2 Hz, 2H), 1.80-1.72 (m, 2H), 1.42-1.27 (m, 2H).

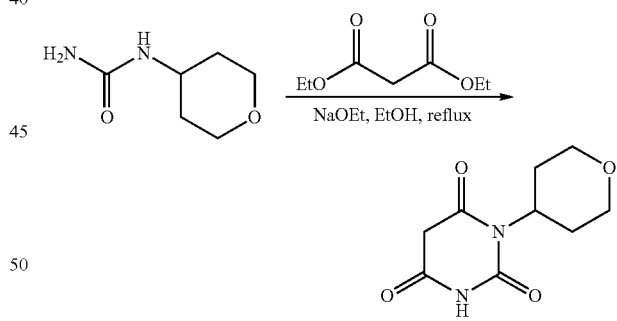

Compound 4.2. 1-(tetrahydro-2H-pyran-4-yl)pyrimidine-2,4,6(1H,3H,5H)-trione

Compound 4.1. (2.8 g, 19.4 mmol) was dissolved in EtOH (30 mL), and diethyl malonate (2.45 mL, 21.4 mmol, 1.1 equiv.), and NaOEt (7.55 mL, 23.3 mmol, 1.2 eq.) were added. The reaction was stirred at 85° C. overnight, and then was cooled to room temperature. The reaction mixture was diluted with H₂O (5 mL), and excess KHSO₄ was added to saturate the aqueous layer. The reaction mixture was extracted with EtOAc (3×15 mL). The combined organic layers were dried with anhydrous MgSO₄, filtered and concentrated under reduced pressure. The resulting residue was purified by flash chromatography (0-25% MeOH in CH$_2$Cl$_2$) to provide a mixture containing the title compound (1.57 g). LC/MS: m/z (ES−) 211 (M−H)⁻.

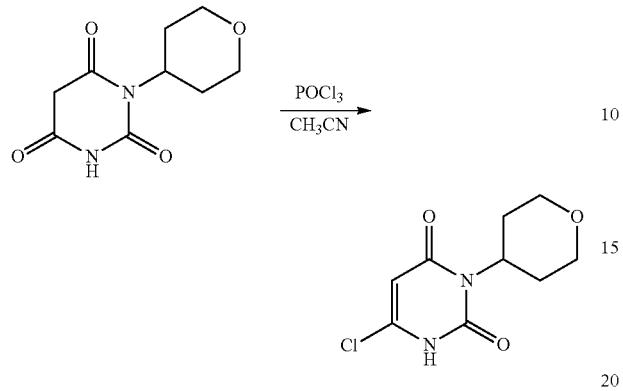

Compound 4.3. 6-chloro-3-(tetrahydro-2H-pyran-4-yl)pyrimidine-2,4(1H,3H)-dione To a solution of 4.2 (1.57 g, 7.4 mmol, 1 equiv.) in CH$_3$CN (15 mL) was added POCl$_3$ (0.551 mL, 5.9 mmol, 0.8 equiv.). The reaction mixture was stirred at 80° C. overnight. An additional aliquot of POCl$_3$ (0.4 eq) was added and the reaction mixture was stirred at 80° C. for 3 h. Additional aliquots of POCl$_3$ (0.4 eq) were added after 3 h and 5 h of stirring at 80° C. The reaction mixture was then stirred at 90° C. for 1 h. The reaction was cooled to room temperature, concentrated, swirled with Et$_2$O (15 mL) and decanted. The resulting residue was rinsed with Et$_2$O (15 mL) and decanted until the Et$_2$O decanted clear. The resulting residue was suspended in MeOH (10 mL) and filtered. The filtrate was concentrated to obtain a mixture of starting material and the desired product 4.3 (~85% pure, 1.6 g). LC/MS: m/z (ES−) 229 (M−H)⁻.

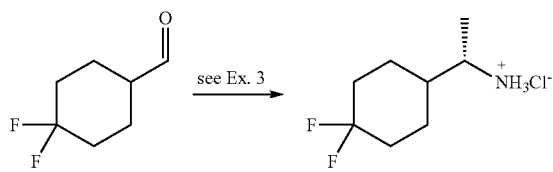

Compound 4.4. (S)-1-(4,4-Difluorocyclohexyl)ethan-1-amine hydrochloride

The title compound was prepared using protocols similar to those used for the preparation of 3.7 (and the subsequent precursors to 3.7) except 4,4-difluorocyclohexane-1-carbaldehyde was used in place of 3.4 to yield a white solid. LC/MS: m/z (ES+) 164 (M+H)⁺. ¹H-NMR (300 MHz, D$_2$O): δ ppm 3.19-3.13 (m, 1H), 2.08-1.96 (m, 2H), 2.35-1.96 (m, 3H), 1.80-1.57 (m, 5H), 1.32-1.20 (m, 2H), 1.13 (d, J=6.0 Hz, 3H).

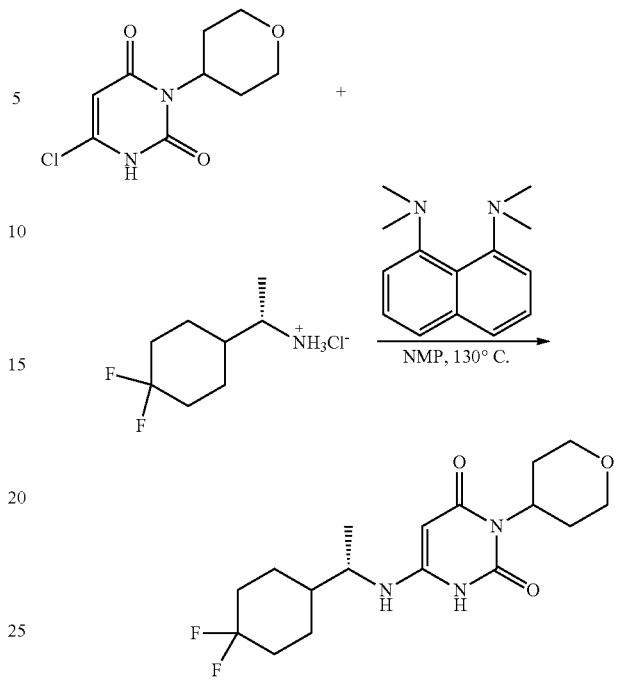

Compound 4. (S)-6-((1-(4,4-difluorocyclohexyl)ethyl)amino)-3-(tetrahydro-2H-pyran-4-yl)pyrimidine-2,4(1H,3H)-dione To a solution of 4.3 (0.455 g, 1.98 mmol, 5.5 equiv) in NMP (5 mL) in a sealed tube were added 4.4, (0.072 g, 0.36 mmol, 1 equiv) and proton sponge (0.184 g, 0.86 mmol, 2.4 equiv.). The reaction mixture was heated to 130° C. for 4 h. The reaction mixture was cooled to room temperature and H$_2$O (30 mL) was added and EtOAc (2×75 mL) was utilized to extract product. The combined organics were concentrated and the resulting residue was purified by preparative RP-HPLC (Shimadzu, Prominence LC-20AP system equipped with a Phenomenex Gemini-NX C18 column, 10-90% CH$_3$CN/H$_2$O in 30 min., 25 mL/min). The fractions containing pure compound were combined and lyophilized to provide 5 mg (4%) of a white solid. LC/MS: m/z (ES+) 358 (M+H)⁺. ¹H NMR (400 MHz, CD$_3$OD): δ ppm 4.95 (partially obscured by solvent, m, 1H), 4.00 (dd, J=11.4, 4.70 Hz, 2H), 3.52-3.34 (m, 3H), 2.72 (m, 2H), 2.15-2.00 (m, 2H), 1.90-1.62 (m, 4H), 1.61-1.24 (m, 5H), 1.17 (d, J=6.7 Hz, 3H).

Example 5

Preparation of (S)-6-((1-(4,4-difluorocyclohexyl)ethyl)amino)-5-fluoro-3-isopropylpyrimidine-2,4(1H,3H)-dione

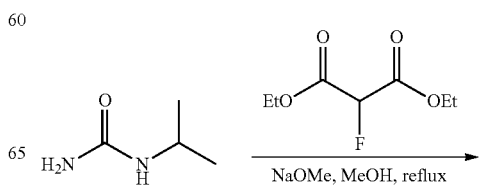

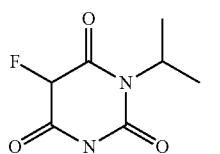

Compound 5.1. 5-Fluoro-1-isopropylpyrimidine-2,4,6(1H,3H,5H)-trione)

To a 100 mL round bottom flask equipped with a reflux condenser and containing a solution of 1.1 (1.31 g, 0.013 mol, 1.00 equiv) in CH$_3$OH (15 mL) were added diethyl fluoromalonate (2.41 g, 0.014 mol, 1.05 equiv) and NaOMe (1.74 g, 0.032 mol, 2.50 equiv). The reaction mixture was stirred for 4 h at 85° C., and then was cooled to 0° C. The reaction mixture was quenched with careful addition of concentrated HCl, adjusting to pH=2 with the addition of excess concentrated HCl. The reaction mixture was then concentrated under reduced pressure. The resulting residue was dried for 18 h under high vacuum to provide 2.65 g (98%) of a white solid. $^1$H-NMR (400 MHz, CDCl$_3$): δ ppm 5.56-5.50 (d, J=24.0 Hz, 1H), 4.91 (m, 2H), 1.46 (m, 6H).

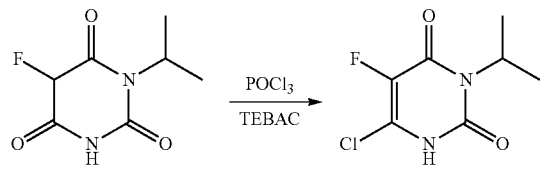

Compound 5.2. 6-Chloro-5-fluoro-3-isopropylpyrimidine-2,4(1H,3H)-dione

To a 100-mL round-bottom flask equiped with a reflux condenser containing 5.1 (2.65 g, 0.014 mmol, 1.00 equiv) were added TEBAC (4.50 g, 0.019 mmol, 1.40 equiv) and POCl$_3$ (25 mL). The reaction mixture was stirred for 4 h at 50° C., then was cooled to room temperature, and concentrated under reduced pressure. The resulting residue was dissolved in CH$_2$Cl$_2$ (50 mL) and H$_2$O (50 mL) was added slowly. The two layers were separated. The organic layer was washed a second time with H$_2$O (100 mL), dried with anhydrous MgSO$_4$, and concentrated under reduced pressure. The resulting residue was purified by flash chromatography (30% EtOAc in hexanes) to yield 2.67 g (58%) of a white solid. $^1$H-NMR (400 MHz, CDCl$_3$): δ ppm 5.19-5.05 (m, 2H), 1.48 (d, J=7.0 Hz, 6H).

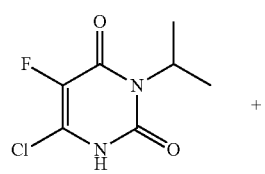

+

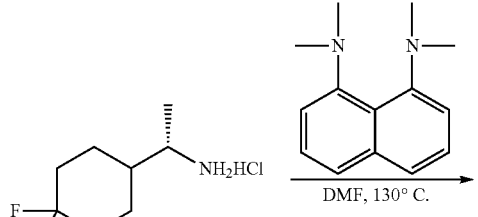

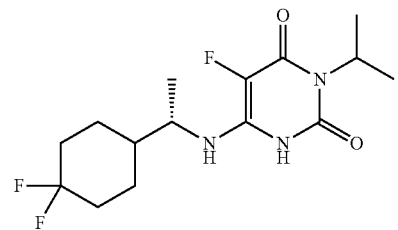

Compound 5. (S)-6-((1-(4,4-difluorocyclohexyl)ethyl)amino)-5-fluoro-3-isopropylpyrimidine-2,4(1H,3H)-dione To a stirred solution of 5.2 (100 mg, 0.4842 mmol) and proton sponge (311 mg, 1.452 mmol) in NMP (1 mL) was added 4.4 (158 mg, 0.9685 mmol). The reaction mixture was plunged into a preheated 130° C. oil and was stirred for 30 minutes. The reaction mixture was cooled to room temperature and diluted with CH$_3$CN:H$_2$O (1:1, 5 mL). The resulting solution was purified by preparative RP-HPLC (Shimadzu, Prominence LC-20AP system equipped with a Phenomenex Gemini-NX C18 column, 20-100% CH$_3$CN/H$_2$O in 40 min., 25 mL/min). The fractions containing pure compound were combined and lyophilized to provide 8 mg (5%) of an off-white solid. LC/MS: m/z (ES+) 334 (M+H)$^+$. $^1$H NMR (400 MHz, CDCl$_3$): δ ppm 8.14 (br s, 1H), 5.15 (m, 1H), 4.47 (br s, 1H), 3.76 (br s, 1H), 2.16 (br s, 2H), 2.00-1.59 (m, 6H), 1.55-1.35 (m, 7H), 1.26 (d, J=6.7 Hz, 3H).

Example 6

Preparation of (S)-6-((1-cyclohexylethyl)amino)-3-isopropylpyrimidine-2,4(1H,3H)-dione (6)

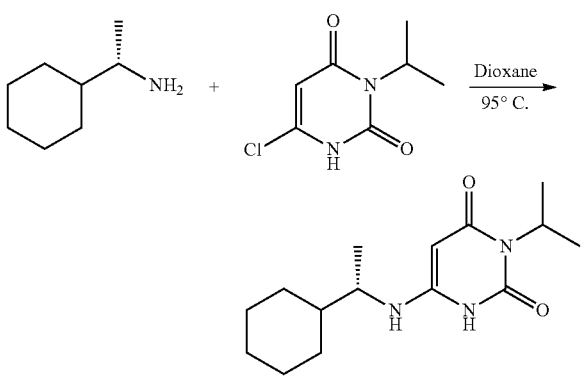

The title compound was prepared using protocols similar to those used for the preparation of 1 except that (S)-cyclohexylethylamine (commercially available, Sigma Aldrich)

was utilized instead of cyclohexylmethanamine. LC/MS: m/z (ES+) 280 (M+H)+. $^1$H-NMR (400 MHz, CDCl$_3$): δ ppm 10.70 (br s, 1H), 5.16 (m, 1H), 4.82 (d, J=2.4 Hz, 1H), 4.64 (br s, 1H), 3.29-3.14 (m, 1H), 1.82-1.62 (m, 5H), 1.43 (m, 7H), 1.31-0.92 (m, 8H).

Example 7

Preparation of 6-((cyclobutylmethyl)amino)-3-isopropylpyrimidine-2,4(1H,3H)-dione (7)

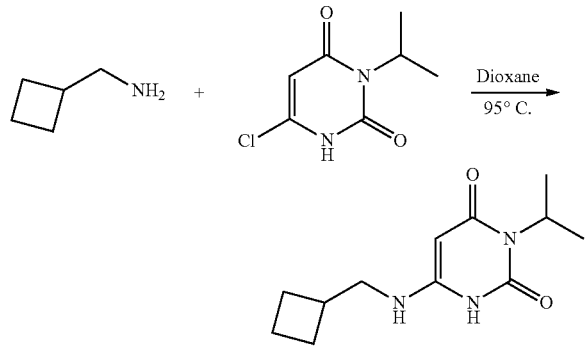

The title compound was prepared using protocols similar to those used for the preparation of 1 except that cyclobutylmethanamine (commercially available, Sigma Aldrich) was utilized instead of cyclohexylmethanamine. LC/MS: m/z (ES+) 238 (M+H)+. $^1$H-NMR (400 MHz, CDCl$_3$): δ ppm 10.53 (br s, 1H), 5.17-5.10 (m, 111), 4.99-4.94 (m, 1H), 4.82 (s, 1H), 3.09 (dd, J=7.0, 5.5 Hz, 2H), 2.60-2.53 (m, 1H), 2.14-2.06 (m, 2H), 1.99-1.84 (m, 2H), 1.77-1.68 (m, 2H), 1.43 (d, J=6.7 Hz, 6H).

Example 8

Preparation of 6-((cycloheptylmethyl)amino)-3-isopropylpyrimidine-2,4(1H,3H)-dione (8)

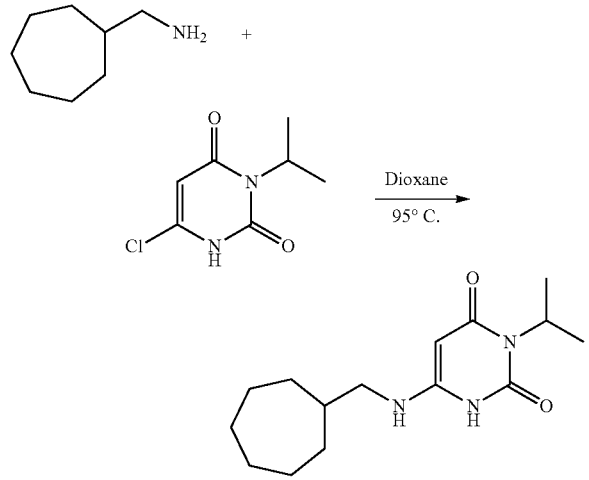

The title compound was prepared using protocols similar to those used for the preparation of 1 except that cycloheptylmethanamine (commercially available, Sigma Aldrich) was utilized instead of cyclohexylmethanamine. LC/MS: m/z (ES+) 280 (M+H)+. $^1$H NMR (400 MHz, CD$_3$OD): δ ppm 5.10-5.03 (m, 1H), 2.91 (d, J=6.7 Hz, 2H), 1.79-1.21 (m, 13H), 1.40 (d, J=7.0 Hz, 6H).

Example 9

Preparation of (S)-6-((1-(4,4-difluorocyclohexyl)ethyl)amino)-3-isopropylpyrimidine-2,4(1H,3H)-dione (9)

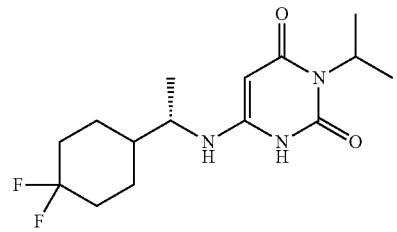 [SMILES: CC(C)n1c(=O)cc(N[C@@H](C)C2CCC(F)(F)CC2)[nH]c1=O]

The title compound was prepared using protocols similar to those used for the preparation of 1 except that 4.4 was utilized instead of cyclohexylmethanamine. LC/MS: m/z (ES+) 316 (M+H)+. $^1$H-NMR (400 MHz, DMSO-d$_6$): δ ppm 9.66 (br s, 1H), 5.90 (d, J=8.8 Hz, 1H), 4.91 (m, 1H), 4.55 (d, J=1.9 Hz, 1H), 3.49-3.14 (m, 1H), 1.97 (br s, 2H), 1.88-1.56 (m, 4H), 1.48 (br s, 1H), 1.34-1.07 (m, 8H), 1.01 (d, J=6.5 Hz, 3H).

Example 10

Preparation of (S)-6-((1-(3,3-difluorocyclobutyl)propan-2-yl)amino)-3-isopropylpyrimidine-2,4(1H,3H)-dione

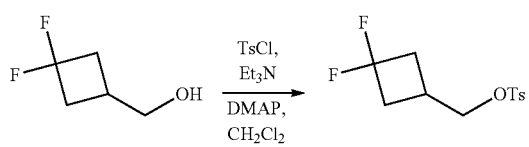

Compound 10.1. (3,3-Difluorocyclobutyl)methyl 4-methylbenzenesulfonate

To a solution of (3,3-difluorocyclobutyl)methanol (500 mg, 4.09 mmol, 1.00 equiv), triethylamine (662.6 mg, 6.55 mmol, 1.60 equiv), and 4-dimethylaminopyridine (750 mg, 6.14 mmol, 1.50 equiv) in CH$_2$Cl$_2$ (5 mL) under argon at 0° C. was added 4-methylbenzene-1-sulfonyl chloride (1.01 g, 5.30 mmol, 1.30 equiv) in portions. The resulting mixture was stirred overnight at ambient temperature. The mixture was then diluted with H$_2$O (20 mL) and extracted with EtOAc (3×20 mL). The combined organic layers were dried with anhydrous Na$_2$SO$_4$ and concentrated under reduced pressure. The crude residue was purified using flash column chromatography (silica gel, EtOAc/Hexanes (1:5)) to yield 1.1 g (97%) of a light yellow oil. $^1$H-NMR (300 MHz, CDCl$_3$): δ ppm 7.77 (d, J=7.6 Hz, 2H), 7.34 (d, J=8.0 Hz, 2H), 4.03 (d, J=6.5 Hz, 2H), 2.75-2.50 (m, 2H), 2.50-2.36 (m, 4H), 2.36-2.08 (m, 2H).

Compound 10.2.
2-(3,3-Difluorocyclobutyl)acetonitrile

A mixture of 10.1 (100 mg, 0.36 mmol, 1.00 equiv) and sodium cyanide (CAUTION: CYANIDE-CONTAINING REACTION), 53.3 mg, 1.09 mmol, 3.00 equiv) in DMSO (3 mL) was stirred under argon at 130° C. After 1.5 h, the mixture was cooled with a water/ice bath and then diluted with $H_2O$ (30 mL). The resulting solution was extracted with EtOAc (3×30 mL). The combined organic layers were dried with anhydrous $Na_2SO_4$ and concentrated under reduced pressure to yield a yellow oil (75 mg) which was used directly in the next step without purification. $^1$H-NMR (300 MHz, $CDCl_3$): δ ppm 2.82-2.70 (m, 2H), 2.55-2.49 (m, 3H), 2.45-2.23 (m, 2H).

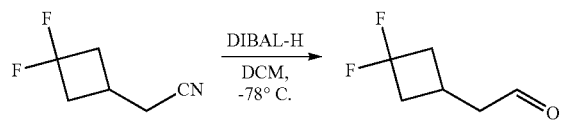 [SMILES: N#CCC1CC(F)(F)C1 ; O=CCC1CC(F)(F)C1]

Compound 10.3.
2-(3,3-Difluorocyclobutyl)acetaldehyde

To a stirred solution of 10.2 (50 mg, 0.38 mmol, 1.00 equiv) in $CH_2Cl_2$ (2 mL) under argon at −78° C. was added dropwise diisobutylaluminum hydride (1.53 mL, 1.53 mmol, 1 M in hexane, 4.0 eq). After stirring at −78° C. for 2 h, the reaction was carefully quenched by the addition of $H_2O$ (5 mL). The resulting mixture was extracted with EtOAc (3×10 mL). The combined organic layers were dried with anhydrous $Na_2SO_4$ and concentrated under reduced pressure to yield 40 mg (78%) of a yellow solid which was used directly in the next step without purification.

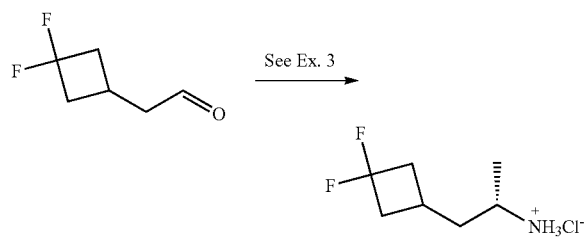

Compound 10.4.
(S)-1-(3,3-Difluorocyclobutyl)propan-2-amine hydrochloride The title compound was prepared using protocols similar to those used for the preparation of 3.7 (and the subsequent precursors to 3.7) except 10.3 was utilized in place of 3.4 to yield a white solid. LC/MS: m/z (ES+) 150 (M+H)$^+$. $^1$H-NMR (300 MHz, $D_2O$): δ ppm 3.39-3.02 (m, 1H), 2.79-2.49 (m, 2H), 2.35-1.96 (m, 3H), 1.96-1.56 (m, 2H), 1.19 (d, J=6.6 Hz, 3H).

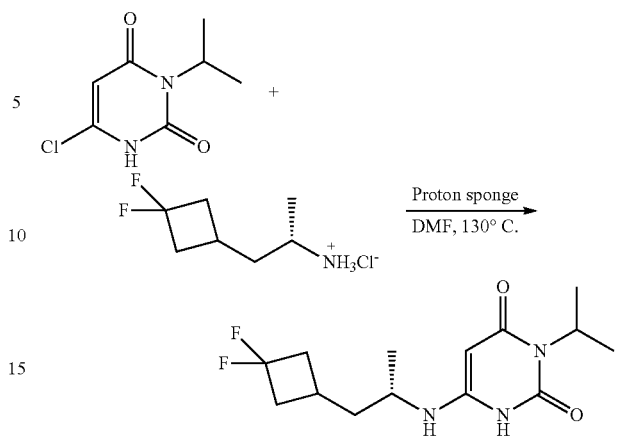

Compound 10. (S)-6-((1-(3,3-difluorocyclobutyl)propan-2-yl)amino)-3-isopropylpyrimidine-2,4(1H,3H)-dione The title compound was prepared using protocols similar to those used for the preparation of 5 except that 1.3 was utilized instead of 5.2 and 10.4 was utilized instead of 4.4. LC/MS: m/z (ES+) 302 (M+H)$^+$. $^1$H-NMR (400 MHz, DMSO-$d_6$): 6 ppm 9.78 (br s, 1H), 5.89 (d, J=8.3 Hz, 1H), 4.97 (m, 1H), 4.55 (s, 1H), 3.50-3.27 (m, 1H), 2.78-2.57 (m, 2H), 2.30-2.17 (m, 2H), 2.15 (br s, 1H), 1.79-1.51 (m, 2H), 1.32 (d, J=6.8 Hz, 6H), 1.09 (d, J=6.3 Hz, 3H).

Example 11

Preparation of (S)-6-((1-(4,4-difluorocyclohexyl)propan-2-yl)amino)-3-(3,5-difluorophenyl)pyrimidine-2,4(1H,3H)-dione

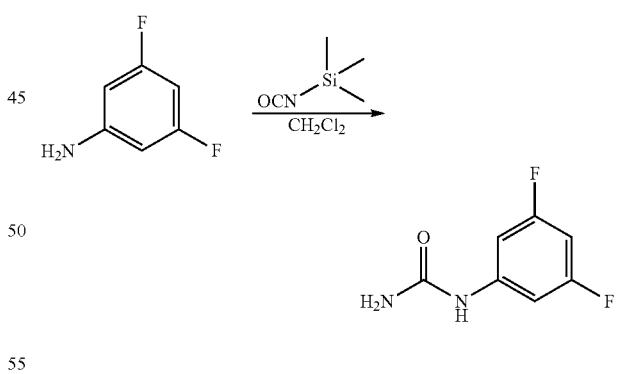

Compound 11.1. 1-(3,5-difluorophenyl)urea

To a stirred solution of 3,5-difluoroaniline (4.0 g, 31 mmol, 1.00 equiv) in $CH_2Cl_2$ (50 mL) under argon at room temperature was added dropwise trimethylsilyl isocyanate (3.56 g, 30.90 mmol, 1.00 equiv). The reaction mixture was stirred overnight and quenched by the dropwise addition of $CH_3OH$ (50 mL). The reaction mixture was concentrated under reduced pressure and the resulting residue was purified by silica gel column chromatography using $CHCl_3/CH_3OH$ (10:1 to 7:1) as eluent to yield the title compound (2.0 g, 38%)

as a white solid. $^1$H-NMR (400 MHz, DMSO-$d_6$): δ ppm 8.96 (s, 1H), 7.16-7.10 (m, 2H), 6.72-6.66 (m, 1H), 6.07 (br s, 2H).

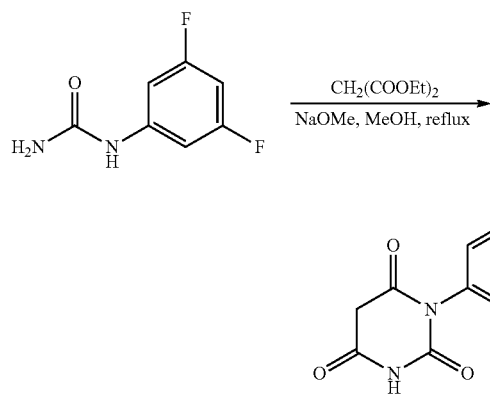

Compound 11.2. 1-(3,5-difluorophenyl)pyrimidine-2,4,6(1H,3H,5H)-trione

To a stirred solution of 11.1 (1.6 g, 0.0093 mol, 1.1 equiv) in CH$_3$OH (20 mL) were added diethyl malonate (1.4 g, 0.0087 mol, 1.0 equiv) and sodium methoxide (1.25 g, 0.0231 mol, 2.7 equiv). The resulting mixture was stirred overnight at 65° C. After cooling to ambient temperature, the pH was carefully adjusted to 5 using 1N HCl. The resulting solution was extracted with EtOAc (3×50 mL). The organic layers were combined and concentrated under reduced pressure. The residue was washed with CH$_3$OH (50 mL) and the resulting solid was filtered to afford 700 mg (31%) of the title compound as a white solid. $^1$H-NMR (400 MHz, DMSO-$d_6$): δ ppm 11.66 (s, 1H), 7.43-7.35 (m, 1H), 7.11-7.08 (m, 2H), 3.77 (s, 2H).

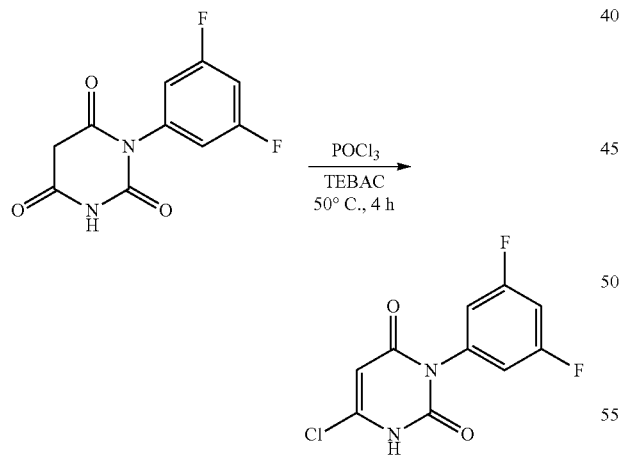

Compound 11.3. 6-chloro-3-(3,5-difluorophenyl)pyrimidine-2,4(1H,3H)-dione

To a 25-mL round-bottom flask containing 11.2 (740 mg, 3.08 mmol, 1.00 equiv) under argon were added triethylbenzylammonium chloride (840 mg, 1.20 equiv) and POCl$_3$ (3 mL). The resulting solution was stirred for 4 h at 50° C. The reaction cooled and quenched by the careful addition of water/ice (20 mL). The pH value of the solution was adjusted to 5 with 2N NaOH. The resulting solution was extracted with EtOAc (2×10 mL) and the organic layers combined. The organic layer was washed with brine (10 mL), dried over anhydrous MgSO$_4$, filtered and then concentrated under reduced pressure. This resulted in 500 mg (crude) of the title compound as a white solid which was used without further purification. $^1$H-NMR (400 MHz, DMSO-$d_6$): δ ppm 12.60 (br, 1H), 7.38-7.32 (m, 1H), 7.21-7.16 (m, 2H), 6.05 (s, 1H).

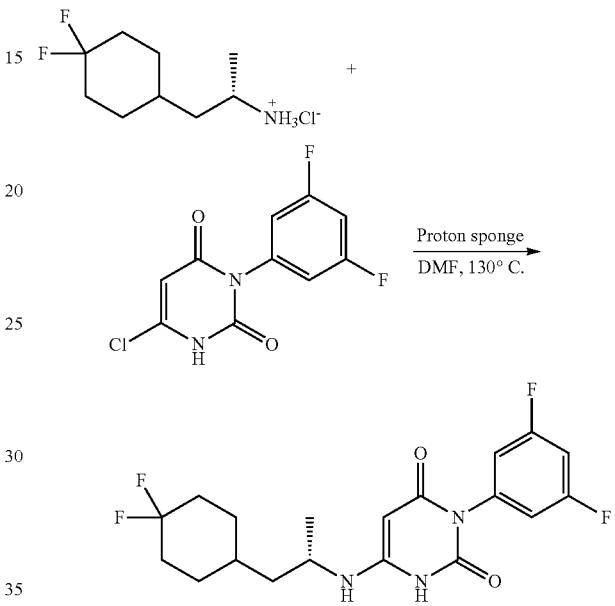

Compound 11. (S)-6-((1-(4,4-difluorocyclohexyl)propan-2-yl)amino)-3-(3,5-difluorophenyl)pyrimidine-2,4(1H,3H)-dione The title compound was prepared using protocols similar to those used for the preparation of 5 except that 11.3 was utilized instead of 5.2 and 3.7 was utilized instead of 4.4. LC/MS: m/z (ES+) 400 (M+H)$^+$. $^1$H-NMR (400 MHz, CDCl$_3$): δ ppm 9.94 (br s, 1H), 6.93-6.87 (m, 1H), 6.83-6.81 (m, 2H), 5.02 (br s, 1H), 3.46 (m, 1H), 2.12-2.06 (m, 2H), 1.71-1.59 (m, 3H), 1.41-1.20 (m, 6H), 1.15 (d, J=6.3 Hz, 3H).

Example 12

Preparation of (S)-6-((1-(3,3-difluorocyclobutyl)propan-2-yl)amino)-3-(3,5-difluorophenyl)pyrimidine-2,4(1H,3H)-dione (12)

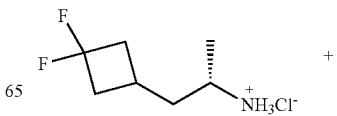

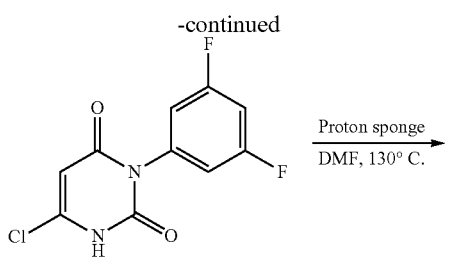

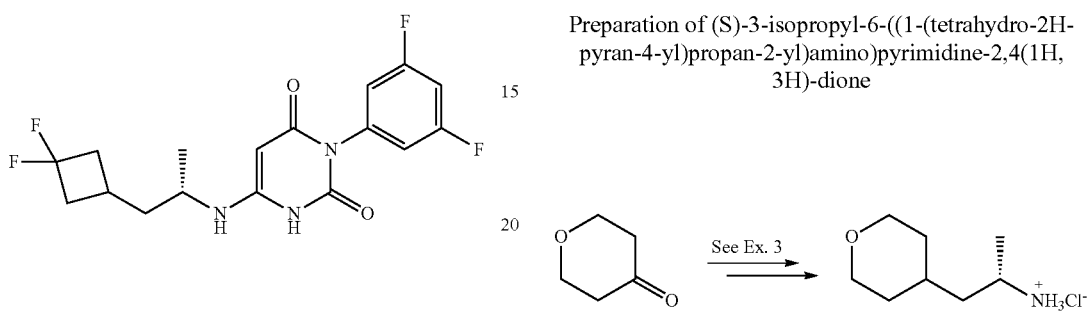

The title compound was prepared using protocols similar to those used for the preparation of 5 except that 11.3 was utilized instead of 5.2 and 10.4 was utilized instead of 4.4. LC/MS: m/z (ES+) 372 (M+H)+. 1H-NMR (400 MHz, CDCl3): δ ppm 10.30 (s, 1H), 6.88 (tt, J=8.8, 2.4 Hz, 1H), 6.81 (dd, J=7.0, 2.4 Hz, 2H), 5.17 (s, 1H), 4.89 (s, 1H), 3.40-3.23 (m, 1H), 2.76-2.50 (m, 2H), 2.24-2.01 (m, 2H), 1.77-1.53 (m, 2H), 1.10 (d, J=6.3 Hz, 3H).

Example 13

Preparation of 3-isopropyl-6-((2-(tetrahydro-2H-pyran-4-yl)ethyl)amino) pyrimidine-2,4(1H,3H)-dione (13)

The title compound was prepared using protocols similar to those used for the preparation of 1 except that 4-(2-amino-ethyl)tetrahydropyran (commercially available, Combi-Blocks Inc., AM-1001) was utilized instead of cyclohexyl-methanamine. LC/MS: m/z (ES+) 282 (M+H)+. 1H-NMR (400 MHz, DMSO-d6): δ ppm 9.77 (br s, 1H), 5.96 (br s, 1H), 4.99-4.89 (m, 1H), 4.48 (s, 1H), 3.81 (dd, J=10.4, 3.7 Hz, 2H), 3.28-3.19 (m, 2H), 3.03-2.98 (m, 2H), 1.57-1.51 (m, 2H), 1.44-1.37 (m, 2H), 1.28 (d, J=6.7 Hz, 6H), 1.24-1.07 (m, 3H).

Example 14

Preparation of (S)-3-isopropyl-6-((1-(tetrahydro-2H-pyran-4-yl)propan-2-yl)amino)pyrimidine-2,4(1H,3H)-dione

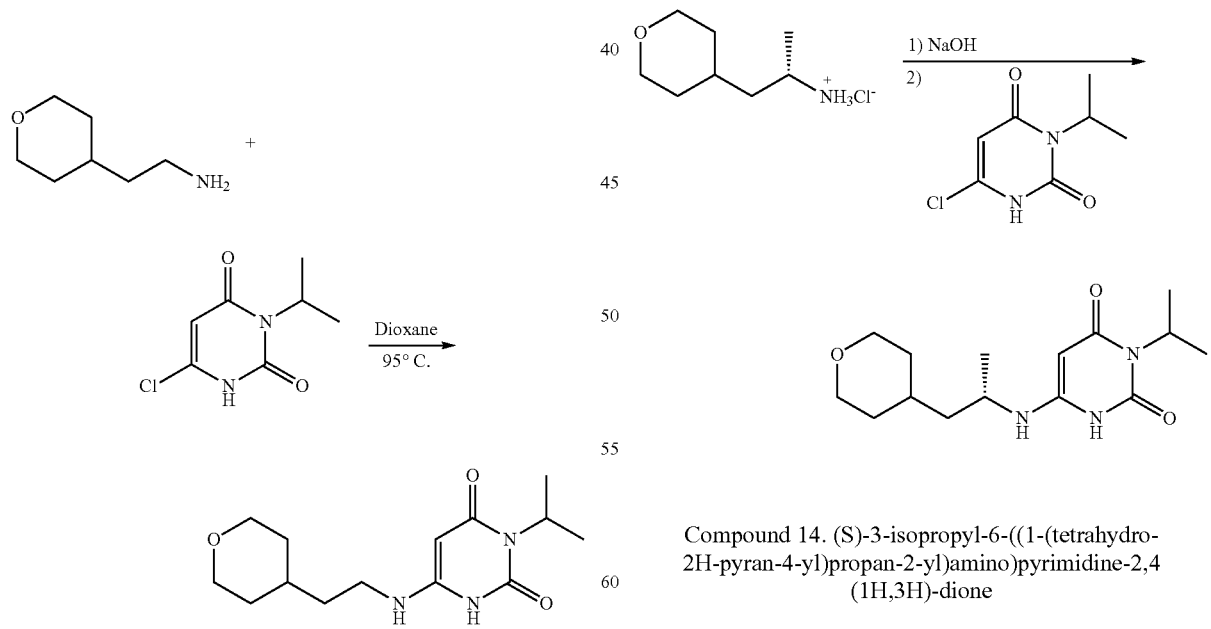

Compound 14.1. (S)-1-(tetrahydro-2H-pyran-4-yl) propan-2-amine hydrochloride

The title compound was prepared using protocols similar to those in Example 3. Here, tetrahydro-4H-pyran-4-one was utilized in place of 4,4-difluorocyclohexan-1-one. LC/MS: m/z (ES+) 144 (M+H)+.

Compound 14. (S)-3-isopropyl-6-((1-(tetrahydro-2H-pyran-4-yl)propan-2-yl)amino)pyrimidine-2,4 (1H,3H)-dione The title compound was prepared using protocols similar to those used for the preparation of 3 except that 14.1 was utilized instead of 3.7. LC/MS: m/z (ES+) 296 (M+H)+. 1H-NMR (300 MHz, DMSO-d6): δ ppm 9.77 (br s, 1H), 5.91 (br s, 1H), 5.00-4.91 (m, 1H), 4.52 (s, 1H), 3.83-3.78 (m, 2H), 3.48-3.44 (m, 1H), 3.30-3.21 (partially obscured, m, 2H), 1.55 (m, 3H), 1.45-1.29 (m, 8H), 1.23-1.19 (m, 2H), 1.12-1.06 (m, 3H).

Example 15

Preparation of (S)-6-((1-cyclohexylethyl)amino)-3-(1-(methylsulfonyl)piperidin-4-yl)pyrimidine-2,4(1H,3H)-dione

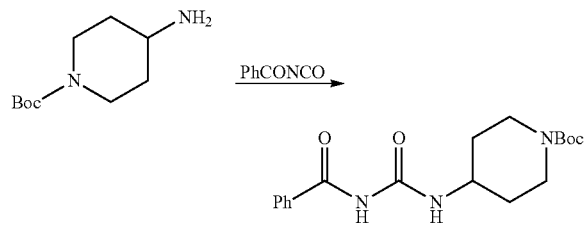

Compound 15.1. tert-Butyl 4-(3-benzoylureido)piperidine-1-carboxylate

To a solution of benzoylisocyanate (4.8 g, 32.6 mmol) in CH$_2$Cl$_2$ (180 mL) at 0° C. was added 4-amino-1-N-boc-piperidine (6.0 g, 30 mmol). The reaction mixture was stirred at room temperature for 4 h and concentrated. The residue was treated with Et$_2$O (100 mL). The precipitate was filtered, washed with Et$_2$O to yield a white solid (5.70 g, yield 55%). LC/MS: m/z (ES+) 337 (M+H)$^+$.

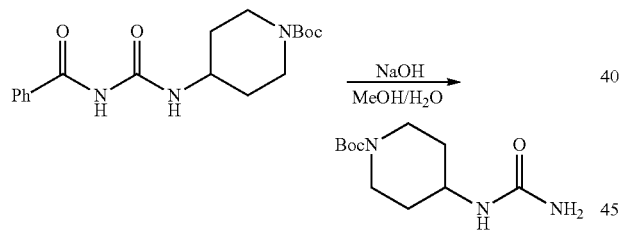

Compound 15.2. tert-Butyl 4-ureidopiperidine-1-carboxylate

To a mixture of 15.1 (5.60 g, 16.1 mmol) in CH$_3$OH (70 ml) and H$_2$O (70 mL) was added sodium hydroxide (11.6 g, 290 mmol) portionwise. The reaction mixture was stirred at room temperature overnight and then refluxed for 1 h. The mixture was cooled to room temperature and concentrated to remove CH$_3$OH. The precipitate was filtered, washed with H$_2$O and dried to yield 3.2 g of a white solid (82%); LC/MS: m/z (ES+) 266 (M+Na)$^+$.

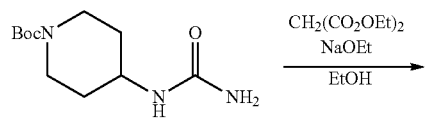

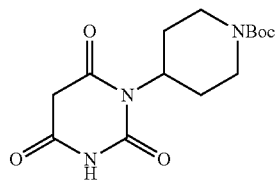

Compound 15.3. tert-Butyl 4-(2,4,6-trioxo-tetrahydropyrimidin-1(2H)-yl)piperidine-1-carboxylate To a mixture of 15.2 (3.63 g, 14.9 mmol), diethylmalonate (2.6 mL, 16.5 mmol) and anhydrous EtOH (60 mL) was added sodium ethoxide (21% in EtOH, 6.6 mL, 17.66 mmol). The mixture was refluxed for 14 h, cooled, and concentrated. The residue was carefully taken up in H$_2$O (15 mL) and washed with EtOAc (2×30 mL). The aqueous layer was separated and the pH was adjusted to 5 with concentrated HCl. The precipitate was filtered, washed with H$_2$O and dried to give 3.70 g (80%) of the title compound as an off-white solid. LC/MS: m/z (ES+) 334 (M+Na)$^+$.

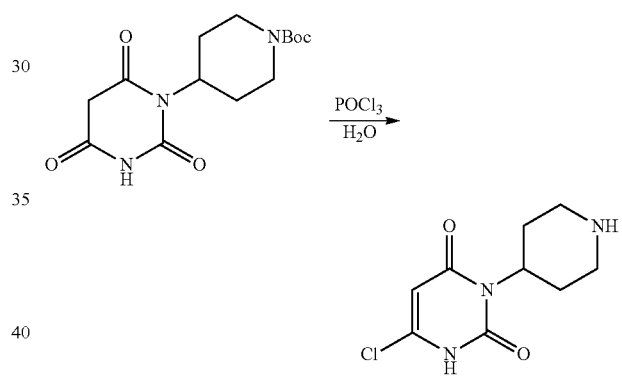

Compound 15.4. 6-chloro-3-(piperidin-4-yl)pyrimidine-2,4(1H,3H)-dione

To a mixture of 15.3 (2.55 g, 8.19 mmol) and POCl$_3$ (10 mL, 100.65 mmol) was added H$_2$O (0.41 mL, 22.78 mmol) dropwise. The mixture was stirred at 120° C. for 30 min, cooled, and then concentrated. The residue was carefully taken up in ice water (20 g). To the mixture was added K$_2$CO$_3$ (~8.0 g) portionwise until the pH was adjusted to 7.0. The precipitate was filtered, washed with H$_2$O (20 mL) and EtOAc (50 mL), dried to yield 1.45 g of an off-white solid (77%). LC/MS: m/z (ES+) 230 (M+H)$^+$.

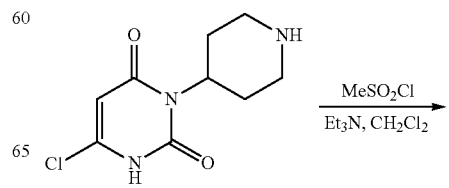

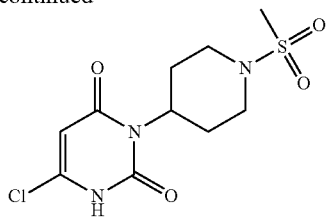

Compound 15.5. 6-chloro-3-(1-(methylsulfonyl)piperidin-4-yl)pyrimidine-2,4(1H,3H)-dione To a mixture of 15.4 (380 mg, 1.65 mmol) and CH$_2$Cl$_2$ (8 mL) was added Et$_3$N (0.70 mL, 4.95 mmol), then methanesulfonyl chloride (0.23 mL, 2.5 mmol). The mixture was stirred at room temperature for 2 h and then quenched with H$_2$O (3 mL) to yield precipitate. The precipitate was filtered and washed with CH$_2$Cl$_2$ (3×3 mL). The filtrate was concentrated to ~1.5 mL. Filtration of a second precipitate was followed by washing with H$_2$O (2×1 mL) and CH$_2$Cl$_2$ (3×2 mL). The precipitates were combined to afford 320 mg of the title compound as an off-white solid. LC/MS: m/z (ES+) 308 (M+H)$^+$.

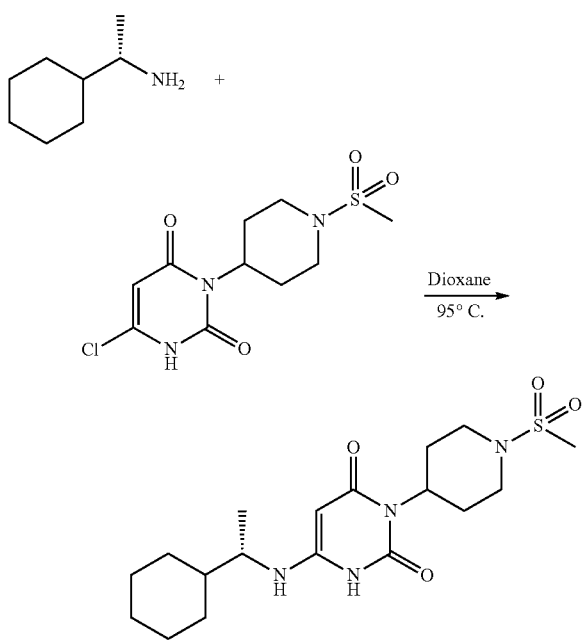

Compound 15. (S)-6-((1-cyclohexylethyl)amino)-3-(1-(methylsulfonyl)piperidin-4-yl)pyrimidine-2,4(1H,3H)-dione The title compound was prepared using protocols similar to those used for the preparation of 6 except that 15.5 was utilized instead of 1.3. LC/MS: m/z (ES+) 399 (M+H)$^+$. $^1$H-NMR (400 MHz, DMSO-d$_6$): δ ppm 9.80 (br s, 1H), 5.97 (br s, 1H), 4.73-4.65 (m, 1H), 4.55 (s, 1H), 3.60 (d, J=11.7 Hz, 2H), 2.85 (s, 3H), 2.77-2.70 (m, 2H), 2.56-2.52 (m, 1H), 1.73-1.65 (m, 3H), 1.60 (d, J=12.5 Hz, 2H), 1.50 (d, J=9.8 Hz, 2H), 1.32 (m, 1H), 1.21-1.08 (m, 4H), 1.01 (d, J=6.7 Hz, 3H), 0.98-0.88 (m, 3H).

Example 16

Myosin Inhibition Assay

Small molecule agents were assessed for their ability to inhibit the enzymatic activity of bovine cardiac myosin using a biochemical assay that couples the release of ADP (adenosine diphosphate) from cardiac myosin to an enzymatic coupling system consisting of pyruvate kinase and lactate dehydrogenase (PK/LDH) and monitoring the absorbance decrease of NADH (at 340 nm) as a function of time. PK converts ADP to ATP (adenosine triphosphate) by converting PEP (phosphoenolpyruvate) to pyruvate. Pyruvate is then converted to lactate by LDH by converting NADH (nicotinamide adenine dinucleotide) to NAD (oxidized nicotinamide adenine dinucleotide). The source of cardiac myosin was from bovine heart in the form of skinned myofibrils. Prior to testing small molecule agents, the bovine myofibrils were assessed for their calcium responsiveness and the calcium concentration that achieves either a 50% (pCa$_{50}$) or 75% (pCa$_{75}$) activation of the myofibril system was chosen as the final condition for assessing the inhibitory activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM12 buffer). Final assay conditions were 1 mg/mL of bovine cardiac myofibrils, 0.4 mM PK/LDH, 50 uM ATP, 0.1 mg/mL BSA (bovine serum albumin), 10 ppm antifoam, 1 mM DTT, 0.5 mM NADH, 1.5 mM PEP at the desired free calcium concentration required to achieve either 50% or 75% activation of the myofibrils.

A dilution series of compound was created in DMSO such that the final desired concentration of compound would be achieved in a volume of 100 µL with a fixed DMSO concentration of 2% (v/v). Typically 2 µL of the dilution series were added to 96 well plate to achieve an 8 or 12 point dose response. Following the addition of 50 µL of a solution containing bovine cardiac myofibrils, PK/LDH and a solution of calcium (that achieved the desired activation), the enzymatic reaction was started with the addition of 50 µL of a solution containing ATP, PEP and NADH. The reaction progress was followed in a Molecular Devices M5e plate reader at ambient temperature using clear half area plates. The plate reader was configured to read absorbance at 340 nm in kinetics mode for 15 minutes. Data were recorded as the slope of the absorbance response to time. The slopes of the absorbance response as a function of time were normalized to slopes on the plate containing DMSO. This normalized rate was then plotted as a function of small molecule concentration and the data was fitted to a four-parameter fit using GraphPad Prism. The midpoint of this plot is the IC50 and is the concentration at which fifty percent of the total response is inhibited. Any agent that failed to achieve a fifty percent inhibition at the highest concentration tested was reported as an IC50 greater than the highest concentration tested (ie. IC50>25 uM).

TABLE 1

Myosin Inhibition Activity of Selected Compounds[a]

| Compound No. | Biochemical Activity (pCa$_{75}$) | Biochemical Activity (pCa$_{50}$) |
| --- | --- | --- |
| 1 | ++ | |
| 2 | + | |
| 3 | +++ | |
| 4 | ++ | |

TABLE 1-continued

Myosin Inhibition Activity of Selected Compounds[a]

| Compound No. | Biochemical Activity (pCa$_{75}$) | Biochemical Activity (pCa$_{50}$) |
|---|---|---|
| 5 | +++ | |
| 6 | +++ | |
| 7 | + | |
| 8 | +++ | |
| 9 | +++ | |
| 10 | ++ | |
| 11 | | +++ |
| 12 | | ++ |
| 13 | + | |
| 14 | ++ | |
| 15 | +++ | |

[a]+++ corresponds to IC50 values below 1 uM. ++ corresponds to IC50 values from 1 to 15 uM. + corresponds to IC50 values above 15 uM.

Selectivity against rabbit skeletal myofibrils was assessed as described above with the exception that the source of myosin was that of fast skeletal myosin from rabbit in the form of myofibrils. Dose responses against rabbit skeletal myofibrils were also determined as described above.

Example 17

Cardiomyocyte Contractility Assay

Contractility of adult rat ventricular myocytes is determined by edge detection with an IonOptix contractility system. Aliquots of myocytes in Tyrode buffer (137 mM NaCl, 3.7 mM KCl, 0.5 mM MgCl$_2$, 1.5 mM CaCl$_2$, 4 mM HEPES, 11 mM glucose) are placed in a perfusion chamber (Series 20 RC-27NE; Warner Instruments), allowed to adhere to the coverslip, and then perfused with 37° C. Tyrode buffer. Myocytes are filed stimulated at 1 Hz and 10V. Only myocytes with clear striations, quiescent prior to pacing, with a cell length of 120-180 microns, a basal fractional shortening equal to 3-8% of the cell length, and a contraction velocity greater than 100 microns per second are used for contractility experiments. To determine the response to compounds, myocytes are first perfused for 60 seconds with Tyrodes buffer followed by 5 minutes of compound and a 140 second washout with Tyrodes buffer. Data is continuously recorded using IonOptix software. Contractility data is analyzed using Ionwizard software (IonOptix). For each cell, 10-20 contractility transients were averaged and compared under basal (no compound) and compound-treated conditions. Compound activity is measured by effects on fractional shortening (FS), where fractional shortening is the ratio of the peak length of the cell at contraction divided by the basal cell length normalized to 100% for an untreated cell.

TABLE 2

Inhibition of Cardiomyocyte Contraction by Selected Compounds[a]

| Compound No. | Activity at 0.3 uM | Activity at 1.0 uM |
|---|---|---|
| 3 | +++ | nd |
| 5 | nd | ++ |
| 9 | nd | +++ |

[a]+ represents fractional shorting inhibition values less than 33%. ++ represents fractional shorting inhibition values from 33% to 66%. +++ represents fractional shortening inhibition values greater than 66%.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having the formula:

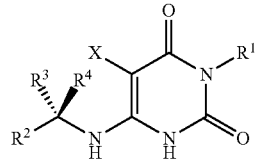

or a pharmaceutically acceptable salt thereof, wherein $R^1$ is a member selected from the group consisting of $C_1$-$C_8$ alkyl, $C_3$-$C_8$ cycloalkyl, $C_3$-$C_8$ cycloalkyl-$C_1$-$C_3$ alkyl, 4- to 7-membered heterocycloalkyl, 4- to 7-membered heterocycloalkyl-$C_1$-$C_3$ alkyl, phenyl, phenyl-$C_1$-$C_3$ alkyl, 5- to 6-membered heteroaryl and 5- to 6-membered heteroaryl-$C_1$-$C_3$ alkyl, wherein each $R^1$ is optionally substituted with from 1-3 $R^a$;

$R^2$ is a member selected from the group consisting of $C_3$-$C_8$ cycloalkyl, $C_3$-$C_8$ cycloalkyl-$C_1$-$C_3$ alkyl, 4- to 7-membered heterocycloalkyl, and 4- to 7-membered heterocycloalkyl-$C_1$-$C_3$ alkyl, wherein each $R^2$ is optionally substituted with from 1-5 $R^b$;

$R^3$ is a member selected from the group consisting of $C_1$-$C_4$ alkyl, $C_3$-$C_4$ cycloalkyl, and 4- to 7-membered heterocycloalkyl wherein each $R^3$ is optionally substituted with from 1-2 $R^c$;

$R^4$ is a member selected from the group consisting of H and $C_1$-$C_4$ alkyl;

or optionally, $R^3$ and $R^4$ are combined with the carbon atom to which each is attached, to form a 3- or 4-membered cycloalkyl or heterocycloalkyl ring;

X is a member selected from the group consisting of H and F;

each $R^a$ is independently selected from the group consisting of halo, CN, hydroxyl, $C_1$-$C_4$ alkyl, $C_1$-$C_4$ haloalkyl, $C_1$-$C_4$ alkoxy, —COR$^{a1}$, —CO$_2$R$^{a1}$, SO$_2$NR$^{a1}$R$^{a2}$, and —CONR$^{a1}$R$^{a2}$, wherein each R$^{a1}$ and R$^{a2}$ is independently selected from the group consisting of H and $C_1$-$C_4$ alkyl or optionally R$^{a1}$ and R$^{a2}$ when attached to a nitrogen atom are combined to form a 4- to 6-membered ring;

each $R^b$ is independently selected from the group consisting of halo, CN, hydroxyl, $C_1$-$C_4$ alkyl, $C_1$-$C_4$ haloalkyl, $C_1$-$C_4$ alkoxy, —COR$^{b1}$, —CO$_2$R$^{b1}$, —SO$_2$R$^{b1}$, —SO$_2$NR$^{b1}$R$^{b2}$, and —CONR$^{b1}$R$^{b2}$, wherein each R$^{b1}$ and R$^{b2}$ is independently selected from the group consisting of H and $C_1$-$C_4$ alkyl or optionally R$^{b1}$ and R$^{b2}$ when attached to a nitrogen atom are combined to form a 4- to 6-membered ring; and each $R^c$ is independently selected from the group consisting of halo, hydroxyl and $C_1$-$C_2$ alkoxy.

2. A compound of claim 1, or a pharmaceutically acceptable salt thereof, wherein $R^1$ is a member selected from the group consisting of $C_1$-$C_8$ alkyl, $C_3$-$C_8$ cycloalkyl, 4- to 7-membered heterocycloalkyl, phenyl, and 5- to 6-membered heteroaryl, wherein each $R^1$ is optionally substituted with from 1-3 $R^a$;

$R^2$ is a member selected from the group consisting of $C_3$-$C_8$ cycloalkyl, $C_3$-$C_8$ cycloalkyl $C_1$-$C_3$ alkyl, and 4- to 7-membered heterocycloalkyl, wherein each $R^2$ is optionally substituted with from 1-5 $R^b$;

$R^3$ is a member selected from the group consisting of H, $C_1$-$C_4$ alkyl, $C_3$-$C_4$ cycloalkyl, and 4- to 7-membered heterocycloalkyl wherein each $R^3$ is optionally substituted with from 1-2 $R^c$;

$R^4$ is a member selected from the group consisting of H and $C_1$-$C_4$ alkyl;

or optionally, $R^3$ and $R^4$ are combined with the carbon atom to which each is attached, to form a 3- or 4-membered cycloalkyl or heterocycloalkyl ring;

and wherein at least one of $R^3$ and $R^4$ is other than H;

X is a member selected from the group consisting of H and F;

each $R^a$ is independently selected from the group consisting of halo, CN, $C_1$-$C_4$ alkyl, $C_1$-$C_4$ alkoxy, $-COR^{a1}$, $-CO_2R^{a1}$, $-SO_2R^{a1}$, $-SO_2NR^{a1}R^{a2}$, and $-CONR^{a1}R^{a2}$, wherein each $R^{a1}$ and $R^{a2}$ is independently selected from the group consisting of H and $C_1$-$C_4$ alkyl or optionally $R^{a1}$ and $R^{a2}$ when attached to a nitrogen atom are combined to form a 4- to 6-membered ring;

each $R^b$ is independently selected from the group consisting of halo, CN, $C_1$-$C_4$ alkyl, $C_1$-$C_4$ alkoxy, $-COR^{b1}$, $-CO_2R^{b1}$, $-SO_2R^{b1}$, $-SO_2NR^{b1}R^{b2}$, and $-CONR^{b1}R^{b2}$, wherein each $R^{b1}$ and $R^{b2}$ is independently selected from the group consisting of H and $C_1$-$C_4$ alkyl or optionally $R^{b1}$ and $R^{b2}$ when attached to a nitrogen atom are combined to form a 4- to 6-membered ring; and each $R^c$ is independently selected from the group consisting of halo and $C_1$-$C_2$ alkoxy.

3. A compound of claim 1, wherein X is H.

4. A compound of claim 1, wherein $R^1$ is selected from the group consisting of $C_3$-$C_4$ alkyl, $C_3$-$C_5$ cycloalkyl, and 4- to 6-membered heterocycloalkyl, wherein each $R^1$ is optionally substituted with from 1-2 $R^a$.

5. A compound of claim 1, wherein $R^1$ is selected from the group consisting of phenyl and 5- to 6-membered heteroaryl, wherein each $R^1$ is optionally substituted with from 1-3 $R^a$.

6. A compound of claim 1, wherein $R^1$ is selected from the group consisting of $C_3$-$C_4$ alkyl, $C_3$-$C_5$ cycloalkyl, and 4- to 6-membered heterocycloalkyl.

7. A compound of claim 1, wherein $R^1$ is 4- to 6-membered heterocycloalkyl, optionally substituted with from 1-2 $R^a$ selected from the group consisting of $C_1$-$C_4$ alkyl, $C_1$-$C_4$ alkoxy, $-COR^{a1}$, $-CO_2R^{a1}$, $-SO_2R^{a1}$, $-SO_2NR^{a1}R^{a2}$, and $-CONR^{a1}R^{a2}$, wherein each $R^{a1}$ and $R^{a2}$ is independently selected from the group consisting of H and $C_1$-$C_4$ alkyl.

8. A compound of claim 1, wherein $R^1$ is selected from the group consisting of cyclobutyl, isopropyl, isobutyl, 1-methoxypropan-2-yl, cyclopentyl, cyclohexyl, 4-tetrahydropyranyl, 1-(methylsulfonyl)piperidin-4-yl, 1-(methoxycarbonyl)piperidin-4-yl, 4,4-difluorocyclohexyl, phenyl, 2-pyridyl, 3-pyridyl, 3-isoxazolyl, 5-isoxazolyl, and 1-methyl-3-pyrazolyl.

9. A compound of claim 1, wherein $R^2$ is selected from the group consisting of $C_4$-$C_6$ cycloalkyl, $C_4$-$C_6$ cycloalkyl $C_1$-$C_2$ alkyl, and 5- to 6-membered heterocycloalkyl, wherein each $R^2$ is optionally substituted with from 1-2 $R^b$.

10. A compound of claim 1, wherein $R^2$ is cyclohexyl, 4,4-difluorocyclohexyl or (4,4-difluorocyclohexyl)methyl.

11. A compound of claim 1, wherein $R^2$ is 4- to 7-membered heterocycloalkyl, which is optionally substituted with from 1-2 $R^b$.

12. A compound of claim 1, wherein $R^3$ is selected from the group consisting of $C_1$-$C_4$ alkyl, $C_1$-$C_4$ alkoxyalkyl, and $C_3$-$C_4$ cycloalkyl.

13. A compound of claim 1, wherein $R^3$ is selected from the group consisting of methyl, ethyl, propyl, cyclopropyl, cyclobutyl and 2-methoxymethyl.

14. A compound of claim 1, wherein $R^3$ is methyl.

15. A compound of claim 1, wherein $R^4$ is H, methyl or ethyl.

16. A compound of claim 1, wherein $R^3$ is methyl and $R^4$ is H.

17. A compound of claim 1, wherein $R^1$ is isopropyl; $R^2$ is selected from the group consisting of $C_4$-$C_6$ cycloalkyl, $C_4$-$C_6$ cycloalkyl $C_1$-$C_2$ alkyl, and 5- to 6-membered heterocycloalkyl, wherein each $R^2$ is optionally substituted with from 1-2 $R^b$; $R^3$ is methyl; and $R^4$ is H.

18. A compound of claim 1, wherein $R^1$ is selected from the group consisting of phenyl and 5- to 6-membered heteroaryl, wherein each $R^1$ is optionally substituted with from 1-3 $R^a$; $R^2$ is selected from the group consisting of $C_4$-$C_6$ cycloalkyl, $C_4$-$C_6$ cycloalkyl-$C_1$-$C_2$ alkyl, and 5- to 6-membered heterocycloalkyl, wherein each $R^2$ is optionally substituted with from 1-2 $R^b$; $R^3$ is methyl; and $R^4$ is H.

19. A pharmaceutical composition comprising a compound of claim 1 and a pharmaceutically acceptable excipient.

20. A compound of claim 1, selected from the group consisting of:

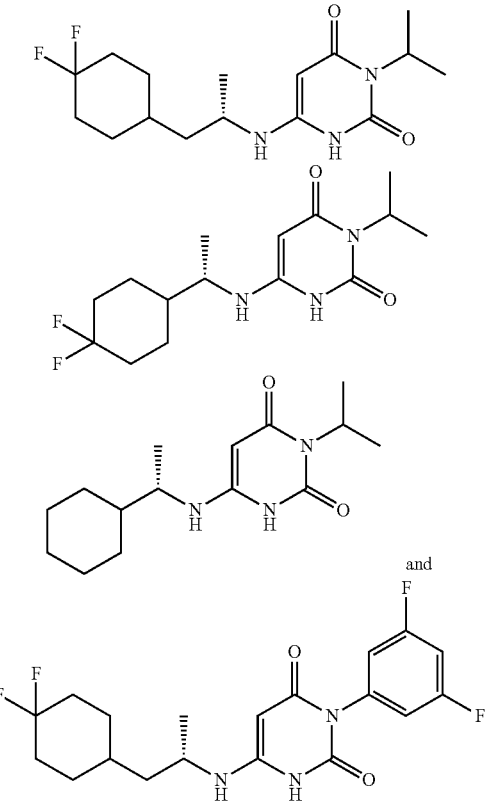

or a pharmaceutically acceptable salt thereof.

* * * * *